US010844407B2

(12) United States Patent
Sato et al.

(10) Patent No.: US 10,844,407 B2
(45) Date of Patent: Nov. 24, 2020

(54) VARIANT TYPE TETRAPRENYL-β-CURCUMENE CYCLASE AND METHOD FOR PRODUCING AMBREIN

(71) Applicants: NIIGATA UNIVERSITY, Niigata (JP); ADEKA CORPORATION, Tokyo (JP)

(72) Inventors: Tsutomu Sato, Niigata (JP); Kotone Okuno, Niigata (JP); Toshihiko Takehana, Tokyo (JP); Seiji Koike, Tokyo (JP)

(73) Assignees: NIIGATA UNIVERSITY, Niigata (JP); ADEKA CORPORATION, Tokyo (JP)

( * ) Notice: Subject to any disclaimer, the term of this patent is extended or adjusted under 35 U.S.C. 154(b) by 0 days.

(21) Appl. No.: 16/080,928

(22) PCT Filed: Mar. 3, 2017

(86) PCT No.: PCT/JP2017/008412
§ 371 (c)(1),
(2) Date: Aug. 29, 2018

(87) PCT Pub. No.: WO2017/150695
PCT Pub. Date: Sep. 8, 2017

(65) Prior Publication Data
US 2019/0078120 A1 Mar. 14, 2019

(30) Foreign Application Priority Data
Mar. 4, 2016 (JP) .................................. 2016-042661

(51) Int. Cl.
*C12P 7/04* (2006.01)
*C12N 9/90* (2006.01)
*C12N 5/10* (2006.01)
*C12N 15/09* (2006.01)
*C12P 7/02* (2006.01)
*C12N 1/20* (2006.01)
*C12N 1/32* (2006.01)
*C12N 9/04* (2006.01)
*C12N 9/88* (2006.01)

(52) U.S. Cl.
CPC .................. *C12P 7/04* (2013.01); *C12N 1/20* (2013.01); *C12N 1/32* (2013.01); *C12N 5/10* (2013.01); *C12N 9/0006* (2013.01); *C12N 9/88* (2013.01); *C12N 9/90* (2013.01); *C12N 15/09* (2013.01); *C12P 7/02* (2013.01); *C12Y 101/01034* (2013.01); *C12Y 402/01137* (2015.07)

(58) Field of Classification Search
CPC . C12N 5/10; C12N 9/90; C12N 15/09; C12N 9/0006; C12N 1/32; C12N 1/20; C12N 9/88; C12P 7/02; C12P 7/04; C12Y 101/01034; C12Y 402/01137
See application file for complete search history.

(56) References Cited

U.S. PATENT DOCUMENTS

2016/0304911 A1 10/2016 Sato et al.
2017/0088824 A1 3/2017 Takehana et al.

FOREIGN PATENT DOCUMENTS

JP          10-236996        9/1998
WO      2015/033746 A1    3/2015
WO      2015/156369 A1    10/2015

OTHER PUBLICATIONS

Banerjee et al., Improving enzymes for bionass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rationalapproaches to engineering enzyme activity: combining the benefits of directedevolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for improving enzyme functions. Appl. Biochem. Biotechnol.,2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

(Continued)

*Primary Examiner* — Ganapathirama Raghu
(74) *Attorney, Agent, or Firm* — Heslin Rothenberg Farley & Mesiti P.C.

(57) ABSTRACT

An object of the present invention is to provide a method for preparing ambrein, which can easily obtain the ambrein. The object can be solved by a mutated tetraprenyl-β-curcumene cyclase wherein a fourth amino acid residue of a DXDD motif, aspartic acid, is substituted with an amino acid other than aspartic acid, (a) having a QXXXGX(W/F) motif, and a QXXXX(G/A)X(F/W/Y) motif on the N-terminal side, and a QXXXGX(F/W/Y) motif, and a QXXXGXW motif and a QXXXGX(F/W) motif on the C-terminal side, and not having a QXXXGXW motif at a position separated by 170 amino acid residues or more on the C-terminal side, with respect to the DXDD motif, (b) having 40% or more identity with the amino acid sequence of SEQ ID NO: 1 or SEQ ID NO: 13, (c) exhibiting ambrein production activity using squalene as a substrate.

16 Claims, 6 Drawing Sheets

Specification includes a Sequence Listing.

(56) References Cited

OTHER PUBLICATIONS

Guo et al., Protein tolerance to random amino acid change. PNAS., 2004, vol. 101 (25): 9205-9210. (Year: 2004).*

Sato, Tsutomu, et al., "Bifunctional Triterpene/Sesquarterpene Cyclase: Tetraprenyl-β-curcumene Cyclase Is Also Squalene Cyclase in *Bacillus megaterium*", *Journal of the American Chemical Society*, vol. 133, pp. 17540-17543 (2011).

Sato, Tsutomu, et al. "Functional Analysis of the DXDDTA Motif in Squalene-Hopene Cyclase by Site-directed Mutagenesis Experiments: Initiation Site of the Polycyclization Reaction and Stabilization Site of the Carbocation Intermediate of the Initially Cyclized A-Ring", *Biosci. Biotechnol. Biochem.*, vol. 63, No. 12, pp. 2189-2198 (1999).

Zhuang, Xun, et al., "Building Terpene Production Platforms in Yeast", *Biotechnology and Bioengineering*, vol. 112, No. 9, pp. 1854-1864 (2015).

Ueda, Daijiro, et al., "Cyclization of Squalene from Both Termini: Identification of an Onoceroid Synthase and Enzymatic Synthesis of Ambrein", *Journal of the American Chemical Society*, vol. 135, pp. 18335-18338 (2013).

Fujiwara, Naoko, et al., "New total synthesis of (+)-ambrein", *Tetrahedron: Asymmetry*, vol. 17, pp. 3037-3045 (2006).

Sato, Tsutomu, et al. "Catalytic Function of the Residues of Phenylalanine and Tyrosine Conserved in Squalene-Hopene Cyclases", *Biosci. Biotechnol. Biochem.*, vol. 65(10), pp. 2233-2242 (2001).

Sato, Tsutomu, et al. "Functional Analyses of Try420 and Leu607 of *Alicyclobacillus acidocaldarius* Squalene-Hopene Cyclase. Neoachillapentaene, a Novel Triterpene with the 1,5,6-Trimethylcyclohexene Moiety Produced through Folding of the Constrained Boat Structure", *Biosci. Biotechnol. Biochem.*, vol. 66(8), pp. 1660-1670.

* cited by examiner

Figure 8

```
WildType   1 MIILLKEVQL EIQRRIAYLR PTQKNDGSFR YCFETGVMPD AFLIMLLRTF DLDKEVLIKQ  60
D373C      1 MIILLKEVQL EIQRRIAYLR PTQKNDGSFR YCFETGVMPD AFLIMLLRTF DLDKEVLIKQ  60

WildType  61 LTERIVSLQN EDGLWTLFDD EEHNLSATIQ AYTALLYSGY YQKNDRILRK AERYIIDSGG 120
D373C     61 LTERIVSLQN EDGLWTLFDD EEHNLSATIQ AYTALLYSGY YQKNDRILRK AERYIIDSGG 120

WildType 121 ISRAHFLTRW MLSVNGLYEW PKLFYLPLSL LLVPTYVPLN FYELSTYARI HFVPMMVAGN 180
D373C    121 ISRAHFLTRW MLSVNGLYEW PKLFYLPLSL LLVPTYVPLN FYELSTYARI HFVPMMVAGN 180

WildType 181 KKFSLTSRHT PSLSHLDVRE QKQESEETTQ ESRASIFLVD HLKQLASLPS YIHKLGYQAA 240
D373C    181 KKFSLTSRHT PSLSHLDVRE QKQESEETTQ ESRASIFLVD HLKQLASLPS YIHKLGYQAA 240

WildType 241 ERYMLERIEK DGTLYSYATS TFFMIYGLLA LGYKKDSFVI QKAIDGICSL LSTCSGHVHV 300
D373C    241 ERYMLERIEK DGTLYSYATS TFFMIYGLLA LGYKKDSFVI QKAIDGICSL LSTCSGHVHV 300

WildType 301 ENSTSTVWDT ALLSYALQEA GVPQQDPMIK GTTRYLKKRQ HTKLGDWQFH NPNTAPGGWG 360
D373C    301 ENSTSTVWDT ALLSYALQEA GVPQQDPMIK GTTRYLKKRQ HTKLGDWQFH NPNTAPGGWG 360

WildType 361 FSDINTNNPD LDDTSAAIRA LSRRAQTDTD YLESWQRGIN WLLSMQNKDG GFAAFEKNTD 420
D373C    361 FSDINTNNPD LDCTSAAIRA LSRRAQTDTD YLESWQRGIN WLLSMQNKDG GFAAFEKNTD 420

WildType 421 SILFTYLPLE NAKDAATDPA TADLTGRVLE CLGNFAGMNK SHPSIKAAVK WLFDHQLDNG 480
D373C    421 SILFTYLPLE NAKDAATDPA TADLTGRVLE CLGNFAGMNK SHPSIKAAVK WLFDHQLDNG 480

WildType 481 SWYGRWGVCY IYGTWAAITG LRAVGVSASD PRIIKAINWL KSIQQEDGGF GESCYSASLK 540
D373C    481 SWYGRWGVCY IYGTWAAITG LRAVGVSASD PRIIKAINWL KSIQQEDGGF GESCYSASLK 540

WildType 541 KYVPLSFSTP SQTAWALDAL MTICPLKDQS VEKGIKFLLN PNLTEQQTHY PTGIGLPGQF 600
D373C    541 KYVPLSFSTP SQTAWALDAL MTICPLKDQS VEKGIKFLLN PNLTEQQTHY PTGIGLPGQF 600

WildType 601 YIQYHSYNDI FPLLALAHYA KKHSS                                      625
D373C    601 YIQYHSYNDI FPLLALAHYA KKHSS                                      625
```

Wild Type: SEQ ID NO:1
D373C: SEQ ID NO:15

Figure 9

VARIANT TYPE TETRAPRENYL-β-CURCUMENE CYCLASE AND METHOD FOR PRODUCING AMBREIN

REFERENCE TO SEQUENCE LISTING

This application contains a Sequence Listing; the file, in ASCII format, is designated 2352082_Sequence Listing_ST25.txt and is 44.5 kilobytes in size. The sequence listing file is hereby incorporated by reference in its entirety into the application.

BACKGROUND ART

Ambergris is a high grade perfume which has been used from around the seventh century, and has been also used as a Chinese medicinal drug. Ambergris is thought to be produced in sperm whales due to lithification of indigestation of foods (octopuses, squids, or the like) by gastrointestinal secretions and excreted. The exact production mechanism of, however, is unknown. The principal component of ambergris is ambrein, and it is considered that ambrein is subject to oxidative decomposition by sunlight and oxygen, while the ambergris is floats on the ocean's surface, thereby producing compounds having a variety of fragrances.

Although ambrein, the principal component of ambergris, is used as perfumes or pharmaceuticals, it is impossible to obtain a large quantity of ambrein is naturally produced. A variety of organic synthesis methods have thus been proposed.

For example, as a method of producing (+)-ambrein easily, efficiently and inexpensively. Patent literature 1 discloses a method comprising a step of producing a new sulfonic acid derivative from ambrenolide and coupling with an optically active γ-cyclogeranyl halide.

Non-patent literature 1 discloses a method of obtaining ambrein by convergent synthesis using a Julia coupling reaction between 2-(1R,2R,4aS,8aS)-2-(methoxymethoxy)-2,5,5,8a-tetramethyldecahydronaphthalene-1-yl) acetaldehyde synthesized from (±)(5,5,8a-trimethyloctahydro-1H-spiro[naphthalene-2,2'-oxirane]-1-yl)methanol and 5-((4-((S)-2,2-dimethyl-6-methylenecyclohexyl)butane-2-yl) sulfonyl)-1-phenyl-1H-tetrazole synthesized from (±)methyl 6-hydroxy-2,2-dimethyl cyclohexanecarboxylate.

However, since conventional organic synthesis methods of ambrein involve many synthesis stages, the reaction systems are complex, and therefore commercialization thereof has not been successful.

CITATION LIST

Patent Literature

[Patent literature 1] Japanese Unexamined Patent Publication (Kokai) No. 10-236996
[Patent literature 2] WO2015/033746

Non-Patent Literature

[Non-patent literature 1] Tetrahedron Asymmetry, (2006) Vol. 17, pp. 3037-3045
[Non-patent literature 2] Biosci. Biotechnol. Biochem., (1999) Vol. 63, pp. 2189-2198
[Non-patent literature 3] Biosci. Biotechnol. Biochem., (2001) Vol. 65, pp. 2233-2242
[Non-patent literature 4] Biosci. Biotechnol. Biochem., (2002) Vol. 66, pp. 1660-1670
[Non-patent literature 5] J. Am. Chem. Soc., (2011) Vol. 133, pp. 17540-17543
[Non-patent literature 6] J. Am. Chem. Soc., (2013) Vol. 135, pp. 18335-18338

SUMMARY OF INVENTION

Technical Problem

A method in which 3-deoxyachilleol A which is a monocyclic triterpene is obtained from squalene by using a mutant enzyme (D377C, D377N, Y420H, Y420W, or the like) of a squalene-hopene cyclase is also known (Non-patent literatures 2 to 4).

The present inventors found that ambrein can be produced by reacting a mutated squalene-papain cyclase capable of producing 3-deoxyachilleol A from squalene with squalene to obtain 3-deoxyacylaol A, and further reacting tetraprenyl-β-curcumene cyclase therewith to produce ambrein (Patent literature 2).

However, the method disclosed in Patent literature 2 is a multi-step reaction. Further, there is also room for improvement in yield.

Accordingly, the object of the present invention is to provide an ambrein-preparation method capable of easily obtaining ambrein.

Solution to Problem

The present inventors conducted intensive studies into a method for efficiently preparing ambrein, and as a result, found that a mutated tetraprenyl-β-curcumene cyclase having a specific mutation has an activity to produce ambrein from squalene. The production of ambrein from squalene is achieved by the mutated tetraprenyl- by the ene intensive studies into a method for effican produce 3-deoxyachilleol A from squalene. The production of ambrein from squalene is achieved by the mutated tetraprenyl- by the rom squalene studies into a method for efficiently preparing alene bbicyclic 8α-hydroxypolypoda-13,17,21-triene. It is surprising that the mutated tetraprenyl-β-curcumene cyclase of the present invention exhibits such enzyme activity.

The present invention is based on the above findings.
Accordingly, the present invention relates to:
[1] a mutated tetraprenyl-β-curcumene cyclase wherein a fourth amino acid residue of a DXDD motif, aspartic acid, is substituted with an amino acid other than aspartic acid,
(a) having a QXXXGX(W/F) motif at a position separated by 100 amino acid residues or more on the N-terminal side, a QXXXX(G/A)X(F/W/Y) motif at a position separated by 10 to 50 amino acid residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, and a QXXXGX(F/W) motif at a position separated by 120 to 170 amino acid residues on the C-terminal side, and not having a QXXXGXW motif at a position separated by 170 amino acid residues or more on the C-terminal side, with respect to the DXDD motif,
(b) having 40% or more identity with the amino acid sequence of SEQ ID NO:1 or SEQ ID NO:13,
(c) exhibiting ambrein production activity using squalene as a substrate,
[2] the mutated tetraprenyl-β-curcumene cyclase of the item [1], wherein a polypeptide constituting the mutated tetraprenyl-β-curcumene cyclase is (1) a polypeptide wherein aspartic acid at position 373 from the N-terminal in the amino acid sequence of SEQ ID NO:1 is substituted with an amino acid other than aspartic acid, or a polypeptide wherein aspartic acid at position 378 from the N-terminal in the amino acid sequence of SEQ ID NO:13 is substituted with an amino acid other than aspartic acid, (2) a polypeptide wherein one or plural amino acids are deleted, substituted, inserted and/or added in the amino acid sequence in which aspartic acid at position 373 from the N-terminal in the amino acid sequence of SEQ ID NO:1 is substituted with an amino acid other than aspartic acid, or aspartic acid at position 378 from the N-terminal in the amino acid sequence of SEQ ID NO:13 is substituted with an amino acid other than aspartic acid, and exhibiting ambrein production activity using squalene as a substrate, (3) a polypeptide having 40% or more identity with the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, (4) a polypeptide comprising the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, (5) a polypeptide comprising the amino acid sequence wherein one or plural amino acids are deleted, substituted, inserted and/or added in the amino acid sequence in which aspartic acid at position 373 from the N-terminal in the amino acid sequence of SEQ ID NO:1 is substituted with an amino acid other than aspartic acid, or the amino acid sequence wherein one or plural amino acids are deleted, substituted, inserted and/or added in the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, or (6) a polypeptide comprising an amino acid sequence having 40% or more identity with the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate,

[3] the mutated tetraprenyl-β-curcumene cyclase of the item [1] or [2], wherein aspartic acid at position 373 from the N-terminal in the amino acid sequence of SEQ ID NO:1 or aspartic acid at position 378 from the N-terminal in the amino acid sequence of SEQ ID NO:13 is substituted with cysteine or glycine,

[4] a polynucleotide encoding the mutated tetraprenyl-β-curcumene cyclase of any one of the items [1] to [3],

[5] a microorganism having the polynucleotide of the item [4],

[6] the microorganism of the item [5] further having a polynucleotide encoding hydroxymethylglutaryl CoA reductase,

[7] a vector comprising a DNA having the polynucleotide of the item [4],

[8] a transformant having the vector of the item [7],

[9] the transformant of the item [7], further having a vector comprising a DNA having a polynucleotide encoding hydroxymethylglutaryl CoA reductase,

[10] a method for preparing ambrein characterized by bringing into contact the mutated tetraprenyl-β-curcumene cyclase of any one of the items claims [1] to [3] with squalene, to obtain ambrein, and

[11] a method for preparing ambrein characterized by culturing the microorganism of the item [5] or [6], or the transformant of the item [8] or [9].

Advantageous Effects of Invention

According to the present invention, ambrein can be synthesized in one step using squalene as a substrate, without a concomitant use of a mutated squalene-hopene cyclase. Further, an ambrein can be efficiently prepared from a carbon source contained in a culture solution by microbial fermentation.

The mutated tetraprenyl-β-curcumene cyclase used in the present invention can produce 3-deoxyachilleol A from squalene. Further, the mutated tetraprenyl-β-curcumene cyclase used in the present invention can produce ambrein from the bicyclic triterpene (8terperoxypolypoda-13,17,21-triene).

BRIEF DESCRIPTION OF THE DRAWINGS

FIG. 8 is a drawing showing amino acid sequences of wild the type tetraprenyl-β-curcumene cyclase (SEQ ID NO:1) and the mutated tetraprenyl-β-curcumene cyclase (SEQ ID NO:15) wherein aspartic acid at position 373 is substituted with cysteine.

FIG. 9 is a drawing showing an alignment of amino acid sequences of tetraprenyl- of amimene cyclase of *Bacillus megaterium* (SEQ ID NO:1), *Bacillus subtilis* (SEQ ID NO:13) and *Bacillus licheniformis* (SEQ ID NO:17), and squalene-hopene cyclase of *Alicyclobacillus acidocaldarius* (SEQ ID NO:18).

DESCRIPTION OF EMBODIMENTS

Figure 1:
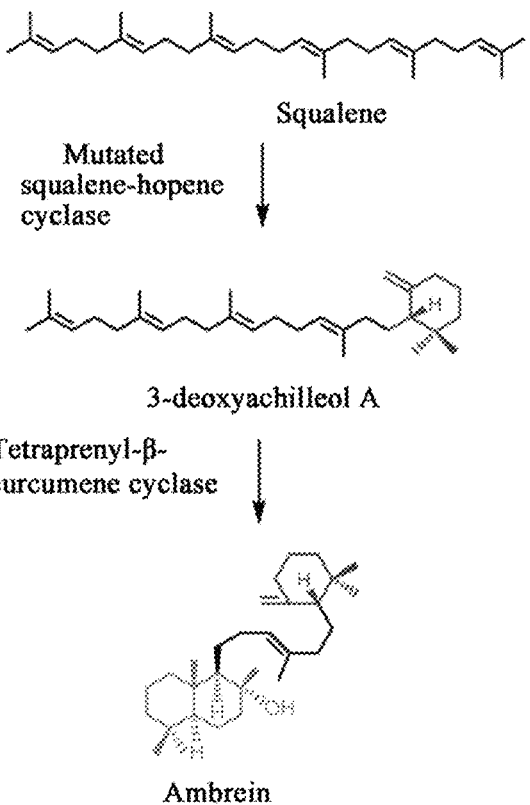
FIG. 1 is a diagram showing a conventional ambrein synthesis pathway using squalene as a substrate, wherein the mutated squalene-hopene cyclase and tetraprenyl-lene-hopene cyclase.

Hereinafter, the present invention will be described in detail.

[1] Mutated Tetraprenyl-β-Curcumene Cyclase

The mutated tetraprenyl-β-curcumene cyclase of the present invention is a mutated tetraprenyl-β-curcumene cyclase wherein a fourth amino acid residue of a DXDD motif, aspartic acid, is substituted with an amino acid other than aspartic acid, and has (a) a QXXGX(W/F) motif at a position separated by 100 amino acid residues or more on the N-terminal side, a QXXXX(G/A)X(F/W/Y) motif at a position separated by 10 to 50 amino acid residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, and a QXXXGX(/W) motif at a position separated by 120 to 170 amino acid residues on the C-terminal side, and does not have a QXXXGXW motif at a position separated by 170 amino acid residues or more on the C-terminal side, with respect to the DXDD motif, and has (b) 40% or more identity with the amino acid sequence of SEQ ID NO:1 or SEQ ID NO:13, and exhibits (c) ambrein production activity using squalene as a substrate.

Alphabets defining each motif or sequence mean one letter amino acid codes, and the character "X" means an arbitrary amino acid. That is to say, in the case of the QXXXGX (W/F) motif, glutamine (Q), any three amino acids (X), glycine (G), any amino acid (X), any one of tryptophan (W) or phenylalanine (F) are arranged from the N terminus to the C terminus. In addition, the wording "having QXXXGX(W/F) motif at a position separated by 100 amino acid residues or more on the N-terminal side with respect to the DXDD motif" means that there are 100 amino acid residues or more between the DXDD motif and the QXXXGX (W/F) motif. Identification of other motifs is similar. Hereinafter, the same applies unless otherwise noted.

According to a preferable embodiment of the mutated tetraprenyl-β-curcumene cyclase of the present invention, a polypeptide constituting the mutated tetraprenyl-β-curcumene cyclase is:

(1) a polypeptide wherein aspartic acid at position 373 from the N-terminal in the amino acid sequence of SEQ ID NO:1 is substituted with an amino acid other than aspartic acid, or a polypeptide wherein aspartic acid at position 378 from the N-terminal in the amino acid sequence of SEQ ID NO:13 is substituted with an amino acid other than aspartic acid, (2) a polypeptide wherein one or plural amino acids are deleted, substituted, inserted and/or added in the amino acid sequence in which aspartic acid at position 373 from the N-terminal in the amino acid sequence of SEQ ID NO:1 is substituted with an amino acid other than aspartic acid, or aspartic acid at position 378 from the N-terminal in the amino acid sequence of SEQ ID NO:13 is substituted with an amino acid other than aspartic acid, and exhibiting ambrein production activity using squalene as a substrate, (3) a polypeptide having 40% or more identity with the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, (4) a polypeptide comprising the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, (5) a polypeptide comprising the amino acid sequence wherein one or plural amino acids are deleted, substituted, inserted and/or added in the amino acid sequence in which aspartic acid at position 373 from the N-terminal in the amino acid sequence of SEQ ID NO:1 is substituted with an amino acid other than aspartic acid, or the amino acid sequence wherein one or plural amino acids are deleted, substituted, inserted and/or added in the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate, or (6) a polypeptide comprising an amino acid sequence having 40% or more identity with the amino acid sequence in which aspartic acid at position 373 from the N-terminal in the amino acid sequence of SEQ ID NO:1 is substituted with an amino acid other than aspartic acid, or the amino acid sequence in which aspartic acid at position 378 from the N-terminal in the amino acid sequence of SEQ ID NO:13 is substituted with an amino acid other than aspartic acid, and exhibiting ambrein production activity using squalene as a substrate.

Further, according to a most preferable embodiment of the mutated tetraprenyl-β-curcumene cyclase of the present invention, the polypeptide constituting the mutated tetraprenyl-β-curcumene cyclase includes a polypeptide consisting of the amino acid sequence of SEQ ID NO:15 which is derived from *Bacillus megaterium*, or a polypeptide consisting of the amino acid sequence of SEQ ID NO:16 which is derived from *Bacillus subtilis*. In the mutated tetraprenyl-β-curcumene cyclase, a fourth amino acid residue of a DXDD motif, aspartic acid, is substituted with cysteine.

(Tetraprenyl-β-Curcumene Cyclase)

The tetraprenyl-β-curcumene cyclase (hereinafter sometimes referred to as a TC) can produce ambrein by using 3-deoxyachilleol A, which comprises a monocycle at one end as a substrate. That is, when 3-deoxyachilleol A is utilized as a substrate, the tetraprenyl-β-curcumene cyclase selectively forms a ring on the end of the 3-deoxyachilleol A on which a ring has not formed to produce a compound which is cyclized at both ends.

Further, the tetraprenyl-β-curcumene cyclase can produce bicyclic 8α-hydroxypolypoda-13,17,21-triene using squalene as a substrate (Non-patent literature 5). Furthermore, the tetraprenyl-β-curcumene cyclase selectively forms a ring on the end of the bicyclic 8α-hydroxypolypoda-13,17,21-triene on which a ring has not been formed to produce a onoceranoxide and 14β-hydroxyonocera-8(26)-en which are cyclized at both ends (Non-patent literature 6).

That is to say, the tetraprenyl-β-curcumene cyclase, which is classified as belonging to EC 4.2.1.129, is an enzyme capable of catalyzing a reaction which produces baciterpenol A from water and tetraprenyl-β-curcumene or a reaction which produces 8α-hydroxypolypoda-13,17,21-triene from squalene.

For example, bacteria such as *Bacillus, Brevibacillus, Paenibacillus*, or *Geobacillus* has the tetraprenyl-β-curcumene cyclase. As the *Bacillus bacterium*, there may be mentioned *Bacillus subtilis, Bacillus megaterium*, or *Bacillus licheniformis*. The tetraprenyl-β-curcumene cyclase has a QXXXGX(W/F) motif at a position separated by 100 amino acid residues or more on the N-terminal side, a QXXXX(G/A)X(F/W/Y) motif at a position separated by 10 to 50 amino acid residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, and a QXXXGX(F/W) motif at a position separated by 120 to 170 amino acid residues on the C-terminal side, with respect to the DXDD motif On the other hand, the tetraprenyl-β-curcumene cyclase does not have the QXXXGXW motif. Further, squalene-hopene cyclase has a GXGFP sequence on the C-terminal side of the QXXXGXW motif, and is characterized in that the fourth amino acid of the DXDD motif is phenylalanine (F). The tetraprenyl-β-curcumene cyclase also has a GXGXP sequence similar to the GXGFP sequence. However, the fourth amino acid is not phenylalanine but, for example, leucine (L), methionine (M), arginine (R) or the like.

(Substitution of Aspartic Acid)

In the mutated tetraprenyl-β-curcumene cyclase (hereinafter sometimes referred to as a mutated TC) of the present invention, for example, aspartic acid at position 373 from the N-terminal in the amino acid sequence of SEQ ID NO:1 is substituted with an amino acid other than aspartic acid, or aspartic acid at position 378 from the N-terminal in the amino acid sequence of SEQ ID NO:15 is substituted with an amino acid other than aspartic acid. The amino acid other than aspartic acid is not limited, as long as the effect of the present invention can be achieved, but includes alanine, cysteine, glutamic acid, phenylalanine, glycine, histidine, isoleucine, lysine, leucine, methionine, asparagine, proline, glutamine, arginine, serine, threonine, valine, tryptophan, or tyrosine. However, it is preferably cysteine or glycine, more preferably cysteine. FIG. 8 shows amino acid sequences of wild type tetraprenyl-β-curcumene cyclase of *Bacillus megaterium* and the mutated tetraprenyl-β-curcumene cyclase in which aspartic acid at position 373 is substituted with cysteine.

The mutated tetraprenyl-β-curcumene cyclase of the present invention can produce 3-deoxyachilleol A from squalene, and can produce ambrein from the bicyclic triterpene (8terpeneom the A f-13,17,21-triene) by substituting aspartic acid at position 373 with an amino acid other than aspartic acid. Further, the mutated tetraprenyl-β-curcumene cyclase of the present invention can produce 3-deoxyachilleol A from squalene, and can produce ambrein from the bicyclic triterpene (8α-hydroxypolypoda-13,17,21-triene) by substituting aspartic acid at position 378 of the wild type tetraprenyl-β-curcumene cyclase of *Bacillus subtilis* with an amino acid other than aspartic acid (I particular cysteine).

Origin of the mutated tetraprenyl-β-curcumene cyclase of the present invention is not particularly limited, and all tetraprenyl-β-curcumene cyclase can be used. That is, the mutated tetraprenyl-particularly limited, and allpartic acid, cine, lysine, leuche DXDD motif, aspartic acid, is substituted with an amino acid other than aspartic acid (preferably cysteine or glycine), can exhibit the effect of the present invention. In other words, the mutated tetraprenyl-. etraprenyl-particuwherein a fourth amino acid residue of a DXDD motif, aspartic acid, is substituted with an amino acid other than aspartic acid (preferably cysteine or glycine), having a QXXXGX(W/F) motif at a position separated by 100 amino acid residues or more on the N-terminal side, a QXXXX(G/A)X(F/W/Y) motif at a position separated by 10 to 50 amino acid residues on the N-terminal side, a QXXXGX(F/W/Y) motif at a position separated by 20 to 50 amino acid residues on the C-terminal side, a QXXXGXW motif at a position separated by 50 to 120 amino acid residues on the C-terminal side, and a QXXXGX(F/W) motif at a position separated by 120 to 170 amino acid residues on the C-terminal side, and not having a QXXXGXW motif at a position separated by 170 amino acid residues or more on the C-terminal side, with respect to the DXDD motif, can exhibit the effect of the present invention. For example, the amino acid sequence identity of the polypeptide between *Bacillus subtilis* and *Bacillus megaterium* is about 50%. However, as shown in the examples, both enzymes have the feature of the present invention, and thus can produce 3-deoxyachilleol A from squalene and produce ambrein from 8α-hydroxypolypoda-13,17,21-triene. In connection to this, the amino acid sequence of tetraprenyl-β-curcumene cyclase of *Bacillus megaterium* is shown in SEQ ID NO:1, and the amino acid sequence of tetraprenyl-β-curcumene cyclase of *Bacillus subtilis* shown in SEQ ID NO:13.

As shown in FIG. 1, when producing ambrein from squalene, conventionally, squalene is converted to 3-deoxyachilleol A by a mutated squalene-hopene cyclase (hereinafter sometimes referred to as mutated SHC), and then 3-deoxyachilleol A is converted to ambrein by wild type tetraprenyl-e to Atimes cyclase, to produce ambrein (Patent literature 2).

Figure 2:
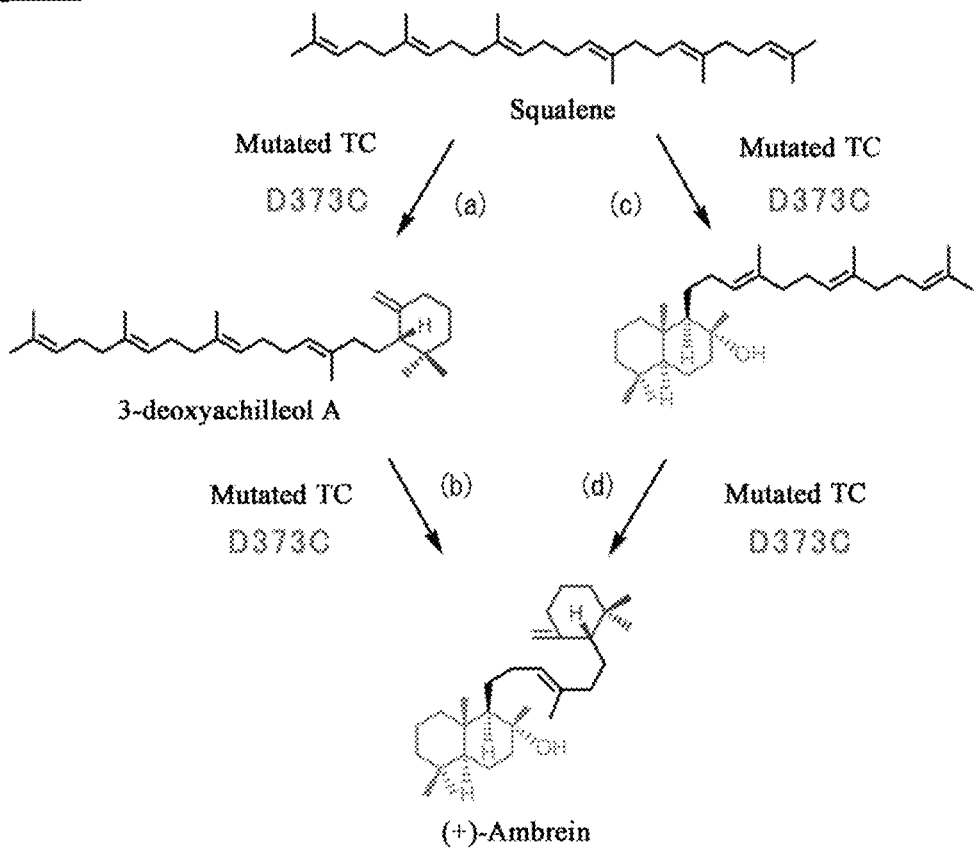
FIG. 2 is a diagram showing two pathways for preparing ambrein from squalene, using the mutated tetraprenyl-β-curcumene cyclase of the present invention.

When ambrein is produced from squalene by using the mutated tetraprenyl-β-curcumene cyclase of the present invention, it is produced through a pathway with monocyclic 3-deoxyachilleol A as an intermediate (hereinafter sometimes referred to as a monocyclic pathway) and a pathway with 8α-hydroxypolypoda-13,17,21-triene as an intermediate (hereinafter referred to as a bicyclic pathway), as shown in FIG. 2.

(Monocyclic Pathway)

In the monocyclic pathway, the monocyclic 3-deoxyachilleol A is produced from squalene by the mutated TC, and then ambrein is produced from 3-deoxyachilleol A by the mutated TC. The conventional wild type TC can convert 3-deoxyachilleol A to ambrein, but cannot convert squalene to monocyclic 3-deoxyachilleol A. The mutated TC of the present invention can convert squalene to monocyclic 3-deoxyachilleol A. Therefore, as shown in FIG. 2, two reactions, i.e. a conversion of squalene to 3-deoxyachilleol A (reaction (a) in FIG. 2), and a conversion of 3-deoxyachilleol A to ambrein (reaction (b) in FIG. 2) can be carried out by one enzyme.

(Bicyclic Pathway)

In the bicyclic pathway, 8α-hydroxypolypoda-13,17,21-triene is produced from squalene by the mutated TC, and then ambrein is produced from 8α-hydroxypolypoda-13,17,21-triene by the mutated TC. The conventional wild type TC can convert squalene to 8α-hydroxypolypoda-13,17,21-triene, but cannot convert 8α-hydroxypolypoda-13,17,21-triene to ambrein. The mutated TC of the present invention can convert 8α-hydroxypolypoda-13,17,21-triene to ambrein. Therefore, as shown in FIG. 2, two reactions, i.e. a conversion of squalene to 8α-hydroxypolypoda-13,17,21-triene (reaction (c) in FIG. 2), and a conversion of 8α-hydroxypolypoda-13,17,21-triene to ambrein (reaction (d) in FIG. 2) can be carried out by one enzyme.

According to the mutated TC of the present invention, in the process of producing ambrein from squalene, four reactions, i.e. a conversion of squalene to 3-deoxyachilleol A (reaction (a)), a conversion of 3-deoxyachilleol A to ambrein (reaction (b)), a conversion of squalene to 8α-hydroxypolypoda-13,17,21-triene (reaction (c)), and a conversion of 8α-hydroxypolypoda-13,17,21-triene to ambrein (reaction (d) in FIG. 2), can be carried out by one enzyme.

(DXDD Motif)

As mentioned previously, in the mutated tetraprenyl-β-curcumene cyclase of the present invention, substitution at position 373 from the N-terminal in the amino acid sequence of SEQ ID NO:1, or substitution at position 378 from the N-terminal side in the amino acid sequence of SEQ ID NO:13 is present in a region called a DXDD motif. That is, the DXDD motif is located at positions 370 to 373 from the N-terminal side of the amino acid sequence of SEQ ID NO:1, or at positions 375 to 378 from the N-terminal side of the amino acid sequence of SEQ ID NO:12. The substitution of amino acid at position 373 or 378 from the N-terminal side is the substitution of aspartic acid, which is the fourth amino acid residue from the N-terminal side of the DXDD motif, with an amino acid other than aspartic acid. The above aspartic acid of the DXDD motif is extremely highly conserved, and the fourth amino acid residue from the N-terminal side thereof is usually aspartic acid. In the present invention, it has been found that, the tetraprenyl-β-curcumene cyclase has an ambrein production activity using squalene as a substrate, by mutating this specific amino acid with high conservation.

(Amino Acid Sequence in which One or Plural Amino Acids are Deleted, Substituted, Inserted and/or Added)

A polypeptide of the mutated tetraprenyl-β-curcumene cyclase of the present invention, may be a polypeptide consisting of an amino acid sequence wherein one or plural amino acids are deleted, substituted, inserted and/or added in the amino acid sequence of SEQ ID NO:1 or 13. The polypeptide exhibits an ambrein production activity using squalene as a substrate. That is, a polypeptide which does not exhibit an ambrein production activity using squalene as a substrate, is not comprised in the polypeptide of the mutated tetraprenyl-β-curcumene cyclase of the present invention. The term "amino acid sequence in which one or plural amino acids are deleted, substituted, inserted and/or added" as used herein means an amino acid sequence modified by amino acid substitution or the like. The number of amino acid modifications can be, for example, 1 to 330, 1 to 300, 1 to 250, 1 to 200, 1 to 150, 1 to 100, or 1 to 50, preferably is 1 to 30, more preferably 1 to 10, still more preferably 1 to 5, most preferably 1 to 2. An example of the modified amino acid sequence of the mutated peptide which can be used in the present invention is preferably an amino acid sequence in which the amino acid has one or plural (preferably 1, 2, 3 or 4) conservative substitutions.

(Amino Acid Sequence Having 40% or More Identity with the Amino Acid Sequence)

A polypeptide of the mutated tetraprenyl-β-curcumene cyclase of the present invention, may be a polypeptide consisting of an amino acid sequence having 40% or more identity with the amino acid sequence of SEQ ID NO:1 or 13. The polypeptide exhibits an ambrein production activity using squalene as a substrate. That is, a polypeptide which does not exhibit an ambrein production activity using squalene as a substrate, is not comprised in the polypeptide of the mutated tetraprenyl-β-curcumene cyclase of the present invention. The mutated tetraprenyl-β-curcumene cyclase is a polypeptide consisting of an amino acid sequence preferably having an identity of 45% or more, an amino acid sequence more preferably having an identity of 50% or more, an amino acid sequence more preferably having an identity of 60% or more, an amino acid sequence more preferably having an identity of 70% or more, an amino acid sequence more preferably having an identity of 80% or more, an amino acid sequence more preferably having an identity of 90% or more, an amino acid sequence most preferably having an identity of 95% or more, and having an ambrein production activity using squalene as a substrate.

The "amino acid sequence in which one or plural amino acids are deleted, substituted, inserted and/or added" in the amino acid sequence of SEQ ID NO:1 or 13 or "amino acid sequence having 40% or more identity with the amino acid sequence" of SEQ ID NO:1 or 13 means that the amino acid sequence of SEQ ID NO:1 or 13 is substituted. This substitution in the amino acid sequence is a conservative substitution that maintains the function of the mutated tetraprenyl-β-curcumene cyclase of the present invention. The term "conservative substitutions" used herein means that amino acid residue(s) are replaced with different amino acid(s) having similar chemical properties. As for the conservative substitution, there may be mentioned, for example, a substitution of a hydrophobic residue for another hydrophobic residue, or a substitution of a polar residue for another polar residue having the same charge. Amino acids which have similar chemical properties and can be conservatively substituted with each other are known to those skilled in the art. More particularly, as for nonpolar (hydrophobic) amino acids, there may be mentioned, for example, alanine, valine, isoleucine, leucine, proline, tryptophan, phenylalanine, or methionine. As for polar (neutral) amino acids, there may be mentioned, for example, glycine, serine, threonine, tyrosine, glutamine, asparagine, or cysteine. As for basic amino acids having a positive charge, there may be mentioned, for example, arginine, histidine, or lysine. As for acidic amino acids having a negative charge, there may be mentioned, for example, aspartic acid or glutamic acid.

The mutation (substitution) of aspartic acid which is a fourth amino acid residue of a DXDD motif in the mutated tetraprenyl-mino acid residue of a DXDD motif in the be mentan amino acid other than aspartic acid is an active substitution (mutation) for imparting an activity to produce ambrein using squalene as a substrate. However, the above conservative substitution is for maintaining the activity to produce ambrein using squalene as a substrate and can be easily carried out by those skilled in the art.

(Motif of Mutated Tetraprenyl-β-Curcumene Cyclase)

Figure 9:
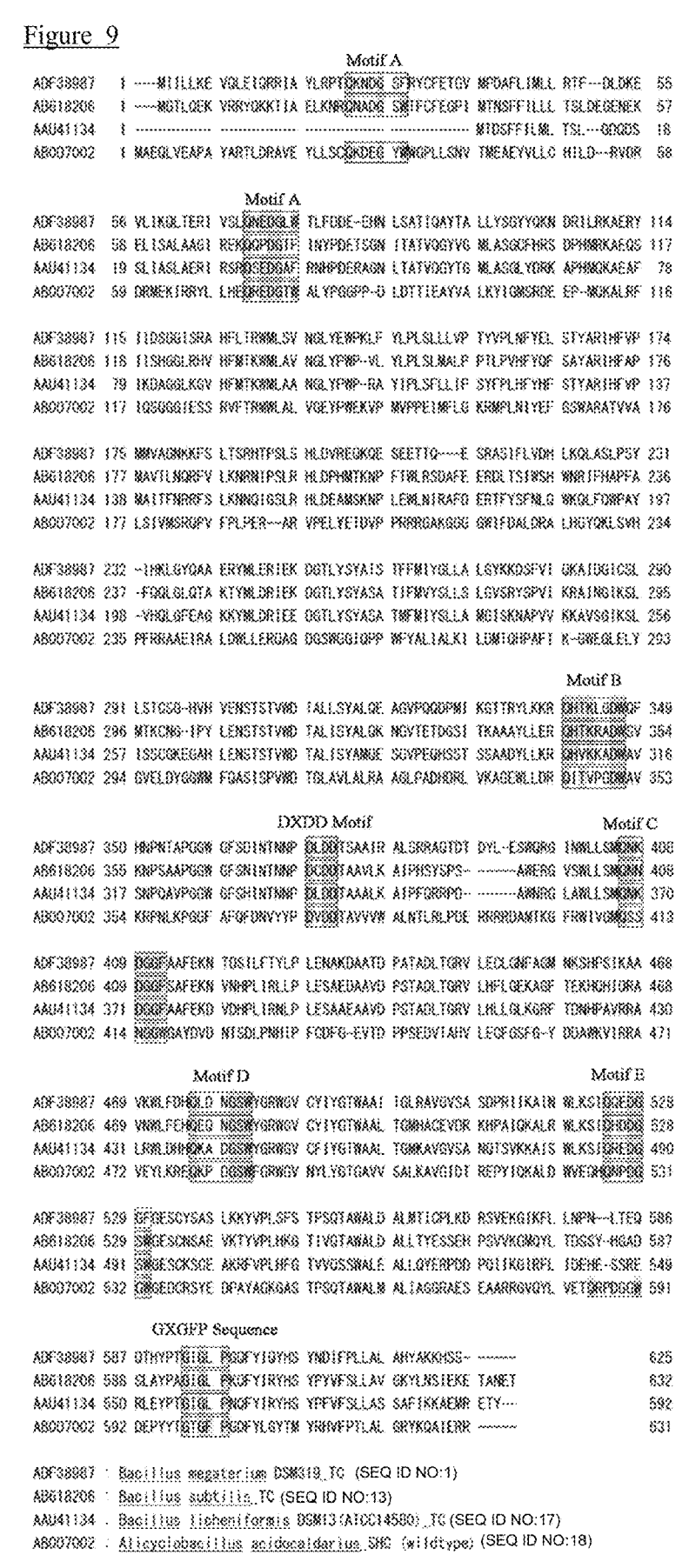

FIG. 9 shows an alignment between tetraprenyl-between tra cyclases of *Bacillus megaterium* (SEQ ID NO:1), *Bacillus subtilis* (SEQ ID NO: 13) and *Bacillus licheniformis* (SEQ ID NO:17), and squalene-hopene cyclase of *Alicy-*

*clobacillus acidocaldarius* (SEQ ID NO:18). The mutated tetraprenyl-β-curcumene cyclase of the present invention has a QXXXGX(W/F) motif (hereinafter sometimes referred to as motif A) at a position separated by 100 amino acid residues or more on the N-terminal side with respect to the DXDD motif. Preferably, it has two motifs A at a position separated by 100 amino acid residues or more on the N-terminal side with respect to the DXDD motif.

Further, it has a QXXXX(G/A)X(F/W/Y) motif (hereinafter sometimes referred to as motif B) at a position separated by 10 to 50 amino acid residues on the N-terminal side with respect to the DXDD motif, and the QXXXX(G/A)X (F/W/Y) motif is preferably QXXXX(G/A)DW motif.

Further, it has a QXXXGX(F/W/Y) motif (hereinafter sometimes referred to as motif C) at a position separated by 20 to 50 amino acid residues on the C-terminal side with respect to the DXDD motif, and the QXXXGX(F/W/Y) motif is preferably QNXXGG(W/F) motif.

Further, it has a QXXXGXW motif (hereinafter sometimes referred to as motif D) at a position separated by 50 to 120 amino acid residues on the C-terminal side with respect to the DXDD motif, and the QXXXGXW motif is preferably QXX(N/D)G(S/A)W motif.

Further, it has a QXXXGX(F/W) motif (hereinafter sometimes referred to as motif E) at a position separated by 120 to 170 amino acid residues on the C-terminal side with respect to the DXDD motif, and the QXXXGX(F/W) motif is preferably QXX(D/N)G(S/G)(F/W) motif.

The mutated tetraprenyl-β-curcumene cyclase of the present invention has the above all motifs A to E in addition to the DXDD motif.

Furthermore, the mutated tetraprenyl-β-curcumene cyclase of the present invention does not have a QXXXGXW motif at a position separated by 170 amino acid residues or more on the C-terminal side with respect to the DXDD motif.

The mutated tetraprenyl-β-curcumene cyclase of the present invention can be obtained using known genetic recombination techniques and the like. For example, a chromosomal DNA of *Bacillus megaterium* is obtained and tetraprenyl-β-curcumene cyclase is amplified by, for example, PCR using appropriate primers. The obtained gene is inserted into an appropriate vector, and the gene sequence is determined. When the fourth amino acid residue from the N-terminal side of the DXDD motif is aspartic acid, a gene encoding the mutated tetraprenyl-β-curcumene cyclase of the present invention can be obtained by introducing mutation to an amino acid other than aspartic acid. The mutated tetraprenyl-β-curcumene cyclase of the present invention can be obtained by incorporating the resulting gene into a host such as yeast and expressing the same.

Further, the tetraprenyl- host such cyclase is known to exist in bacteria such as *Bacillus* in addition to *Bacillus megaterium*, and thus it is possible to obtain an enzyme derived from *Bacillus subtilis* (accession number: AB 618206), and an enzyme derived from *Bacillus licheniformis* (accession number: AAU 41134), and the like.

Further, the gene encoding the mutated tetraprenyl-β-curcumene cyclase of the present invention can be synthesized by a known gene synthesis method such as the method of Khorana et al. (Gupta et al., 1968), the method of Narang et al. (Scarpulla et al., 1982) or the method of Rossi et al. (Rossi et al., 1982). Then, the mutated tetraprenyl-β-curcumene cyclase can be obtained by expressing the resulting synthetic gene.

[2] Polynucleotide

The polynucleotide of the present invention is not particularly limited as long as it is a polynucleotide encoding the tetraprenyl-eotide oft cyclase of the present invention, and there may be mentioned a polypeptide encoding the polypeptide wherein aspartic acid which is the fourth amino acid residue from the N-terminal side of the DXDD motif, is mutated to (substituted with) an amino acid other than aspartic acid.

Specifically, as the polynucleotide of the present invention, there may be mentioned a polynucleotide comprising a sequence consisting of the base sequence of SEQ ID NO:2 or SEQ ID NO:14, which encodes the polypeptide in which the fourth amino acid residue from the N-terminal side of the DXDD motif, aspartic acid, is mutated to (substituted with) cysteine.

Further, there may be mentioned a polynucleotide hybridizing under stringent conditions to the polynucleotide consisting of base sequence of SEQ ID NO:2 and having an ambrein production activity using squalene as a substrate.

In connection to this, the term "polynucleotide" as used herein includes both DNA and RNA.

Further, the polynucleotide of the present invention is preferably changed to base sequence of the optimal codon according to the microorganism or the host cell into which the polynucleotide is introduced.

[3] Microorganism

The microorganism of the present invention has the polynucleotide of the present invention. That is, the microorganism is not particularly limited so long as it includes the polynucleotides of the present invention within cell thereof, and there may be mentioned *Escherichia coli*, *Bacillus subtilis*, *Brevibacillus*, *Actinomycete*, Baker's yeast, *Aspergillus oryzae*, or *Neurospora crassa*.

<<Hydroxymethylglutaryl CoA Reductase>>

Preferably, the microorganism of the present invention further has a polynucleotide encoding the hydroxymethylglutaryl CoA reductase (hereinafter sometimes referred to as HMGR).

HMGR converts hydroxymethylglutaryl CoA into mevalonate in the synthetic route of farnesyl pyrophosphate. Squalene which is a substrate of the mutated tetraprenyl-β-curcumene cyclase of the present invention is produced through the two molecule bonding of farnesyl pyrophosphate. A production of squalene can be increased in microorganisms and a production of ambrein can be increased using microorganisms by enhancing the activity of the hydroxymethylglutaryl CoA reductase.

A polypeptide of the hydroxymethylglutaryl CoA reductase is not particularly limited, so long as it has the activity of the hydroxymethylglutaryl CoA reductase. However, the polypeptide preferably consists of (1) an amino acid sequence of the 514th to 1022nd amino acids in the amino acid sequence of SEQ ID NO:3, (2) an amino acid sequence wherein one or plural amino acids are deleted, substituted, inserted and/or added in the amino acid sequence consisting of the 514th to 1022nd amino acids in the amino acid sequence of SEQ ID NO:3, or (3) an amino acid sequence having 80% or more (preferably 90% or more, more preferably 95% or more) identity with the amino acid sequence consisting of the 514th to 1,022nd amino acids in the amino acid sequence of SEQ ID NO:3, or (1) an amino acid sequence of SEQ ID NO:3, (2) an amino acid sequence wherein one or plural amino acids are deleted, substituted, inserted and/or added in the amino acid sequence of SEQ ID NO:3, or (3) an amino acid sequence having 80% or more identity with the amino acid sequence of SEQ ID NO:3.

The hydroxymethylglutaryl CoA reductase consisting of the above amino acid sequences exhibits an excellent reductase activity. Therefore, the polypeptide comprising the amino acid sequence of the 514th to 1,022nd amino acids in the amino acid sequence of SEQ ID NO:3 is an amino acid sequence excluding the membrane-binding region of hydroxymethylglutaryl CoA reductase, and exhibits an excellent activity of hydroxymethylglutaryl CoA reductase. SEQ ID NO:3 shows an embodiment of nucleotide sequence (base sequence) encoding the hydroxymethylglutaryl CoA reductase.

[4] Vector

The vector of the present invention comprises the DNA having polynucleotide encoding the mutated tetraprenyl-β-curcumene cyclase. That is, the vector of the present invention is not particularly limited, so long as it comprises the polynucleotide of the present invention. As the vector, there may be mentioned, for example, a vector obtained by introducing the polynucleotide of the present invention into a known expression vector appropriately selected in accordance with a host cell to be used.

Preferably, the expression vector is autonomously replicable in the host such as E. coli, or baker's yeast, or can be incorporated into the chromosome, and has a high expression efficiency of the foreign protein. The expression vector for expressing the polynucleotide is autonomously replicable in the microorganism, and is preferably a recombinant vector composed of a promoter, a ribosome binding sequence, the DNA and a transcription termination sequence. Further, it may contain a gene controlling the promoter.

More particularly, as an expression vector, for example, pBTrp2, pBTac1, pBTac2 (three vectors are commercially available from Boehringer Mannheim), pKK233-2 (Pharmacia), pSE280 (Invitrogen), pGEMEX-1 (Promega), pQE-8 (QIAGEN), pQE-30 (QIAGEN), pKYP10 (Japanese Unexamined Patent Publication (Kokai) No. 58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescriptII SK+, pBluescriptII SK (−)(Stratagene), pTrS30 (FERMBP-5407), pTrS32 (FERM BP-5408), pGEX (Pharmacia), pET-3 (Novagen), pTerm2 (U.S. Pat. Nos. 4,686,191, 4,939,094, 5,160,735), pSupex, pUB110, pTP5, pC194, pUC18 [gene, 33, 103 (1985)], pUC19 [Gene, 33, 103 (1985)], pSTV28 (TAKARA), pSTV29 (TAKARA), pUC118 (TAKARA), pPA1 (Japanese Unexamined Patent Publication (Kokai) No. 63-233798), pEG400 [J. Bacteriol., 172, 2392 (1990)], pColdI, pColdII, pColdIII, pColdIV, pNIDNA, pNI-HisDNA (TAKARA BIO) and the like can be exemplified.

As the promoter, any one can be used as long as it can be expressed in host cells such as Escherichia coli, baker's yeast and the like. For example, there may be mentioned a promoter derived from Escherichia coli, phage, or the like, (such as a trp promoter (Ptrp), lac promoter (Plac), PL promoter, PR promoter, or PSE promoter), SPO1 promoter, SPO2 promoter, penP promoter or the like. Further, a promoter designed and modified artificially, such as a promoter (Ptrpx 2) in which two Ptrp are connected in series, tac promoter, let I promoter, or lacT 7 promoter, can also be used. In order to prepare an enzyme for production by an enzymatic method (biosynthesis by in vitro enzymatic reaction using squalene as a substrate), a promoter which functions as a strong promoter and is capable of mass production of a target protein is preferable. In addition, an inducible promoter is more preferable. As the inducible promoter, for example, there may be mentioned a promoter of the cold shock gene cspA which is induced at low temperature, T7 promoter induced by the addition of inducer IPTG, or the like. Further, in a fermentative production (biosynthesis in vivo by a host using glucose or the like as a carbon source), among the above promoters, a promoter capable of constantly expressing a target gene regardless of tissue, i.e., constitutive promoter is more preferable. As the constitutive promoter, there may mentioned a promoter of an alcohol dehydrogenase 1 gene (ADH1), a translation elongation factor TF-1α gene (TEF1), a phosphoglycerate kinase gene (PGK1), a triose phosphate isomerase gene (TPI1), a triose phosphate dehydrogenase gene (TDH3), or a pyruvate kinase gene (PYK1).

[5] Transformant

The transformant of the present invention is not particularly limited, so long as it comprises the polynucleotide of the present invention. The transformant of the present invention may be, for example, a cell in which the polynucleotide is integrated into a chromosome of a host cell, or a transformant containing the polynucleotide as a vector comprising polynucleotide. Further, the transformant of the present invention may be a transformant expressing the polypeptide of the present invention, or a transformant not expressing the polypeptide of the present invention. The transformant of the present invention may be obtained by, for example, transfecting a desired host cell with the vector of the present invention or the polynucleotide of the present invention per se.

The host cell is not particular limited. A strain which is easy to handle, such as Escherichia coli, Bacillus subtilis, Brevibacillus, actinomycete, yeast, Aspergillus oryzae, Neurospora crassais preferable, but insect cells, plant cells, animal cells or the like can be used. However, in order to prepare an enzyme for production by an enzymatic method (biosynthesis by in vitro enzymatic reaction using squalene as a substrate), Escherichia coli, Bacillus subtilis, and Brevibacillus are preferable, and Escherichia coli is most preferable. Further, in a fermentative production (biosynthesis in vivo by a host using glucose or the like as a carbon source), yeast is most preferable. As the most preferable yeast strain, there may be mentioned sake yeast. The sake yeast Kyokai 7, or Kyokai 701 is more preferable. The strain Kyokai K701 is a non-foaming mutant strain bred from wild-type strain Kyokai K7. However, the strain Kyokai K701'K701ir, the strain ng mutant strain bred from wild-type strain Kyokai K7.

In the fermentative production (biosynthesis in vivo by a host using glucose or the like as a carbon source), the transformant of the present invention preferably has the vector comprising DNA having the polynucleotide encoding the hydroxymethylglutaryl CoA reductase. In the production of ambrein using the transformant, an amount of production can be increased by containing the vector. The hydroxymethylglutaryl CoA reductase is described in the above item "Microorganism."

In connection to this, the wording "having the vector containing the polynucleotide encoding the hydroxymethylglutaryl CoA reductase" means that the DNA having the polynucleotide encoding the hydroxymethylglutaryl CoA reductase may be contained in "the vector comprising the DNA having polynucleotide encoding the mutated tetraprenyl-β-curcumene cyclase", or "the vector comprising the DNA having polynucleotide encoding the mutated tetraprenyl-β-curcumene cyclase" and "the vector comprising the DNA having polynucleotide encoding the hydroxymethyl-glutaryl CoA reductase" are prepared respectively and the host cells are transformed thereby.

[6] Method for Preparing Ambrein

The method for preparing ambrein of the present invention is characterized by bringing into contact the mutated tetraprenyl-β-curcumene cyclase with squalene, to obtain ambrein.

The mutated tetraprenyl-β-curcumene cyclase can be prepared by culturing the transformant obtained by introducing the enzyme expression vector into bacteria or the like. The medium used for culturing the transformant may be a commonly used medium and is appropriately selected depending on the type of host. For example, in the case of culturing E. coli, LB medium and the like are used. Antibiotics according to the type of selective marker may be added to the medium.

The mutated tetraprenyl-β-curcumene cyclase may be obtained by extraction followed by purification from a culture medium which has been obtained by culturing a transformant capable of expressing the enzyme. Further, it may be expressed as a fusion protein obtained by fusing a trigger factor (TF), a His tag or the like to the N-terminal side or the C-terminal side of the polypeptide of the mutated tetraprenyl-a fusion protein obtained by fusing a trigger factor (TF), a purification and the like may be facilitated. An extraction liquid containing the enzyme, which has been extracted from a transformant in a culture medium, may be used as it is. As a method of extracting an enzyme from a transformant, a known method may be applied. A step of extracting an enzyme may comprise, for example, crushing a transformant in an extraction solvent and separating cell contents from crushed pieces of the transformant. The obtained cell contents contain the mutated tetraprenyl-β-curcumene cyclase of interest.

As the method of crushing a transformant, a known method in which a transformant is crushed and an enzyme liquid can be recovered may be applied, and examples thereof include ultrasonic crushing and glass beads crushing. The conditions of crushing are not particularly restricted as long as the enzyme is not inactivated, such as a condition of not higher than 10° C. and for 15 minutes.

Examples of the method of separating cell contents from crushed pieces of microorganism include sedimentation, centrifugation, filtering separation, and a combination of two or more thereof. Conditions for these separation methods are known to those skilled in the art. The conditions are, for example, from 8,000×g to 15,000×g and from 10 to 20 minutes in the case of centrifugation.

The extraction solvent may be a solvent which is usually used as a solvent for extracting an enzyme, and examples thereof include Tris-HCl buffer and potassium phosphate buffer. The pH of an extraction solvent is, from the viewpoint of enzyme stability, preferably from 3 to 10 and more preferably from 6 to 8.

The extraction solvent may contain a surfactant. Examples of the surfactant include a nonionic surfactant and an ampholytic surfactant. Examples of the nonionic surfactant include: a polyoxyethylene sorbitan fatty acid ester such as poly(oxyethylene)sorbitan monooleate (Tween 80); alkylglucoside such as n-octylβ-D-glucoside; a sucrose fatty acid ester such as sucrose stearate; and a polyglycerol fatty acid ester such as polyglycerol stearate. Examples of the ampholytic surfactant include N,N-dimethyl-N-dodecylglycine betaine which is an alkylbetaine. Besides the above, surfactants generally used in the art such as Triton X-100 (TRI-TON X-100), polyoxyethylene(20)cetyl ether (BRIJ-58), and nonylphenol ethoxylate (TERGITOL NP-40) can be utilized.

The concentration of a surfactant in an extraction solvent is, from the viewpoint of enzyme stability, preferably from 0.001% by mass to 10% by mass, more preferably from 0.10% by mass to 3.0% by mass, and further preferably from 0.10% by mass to 1.0% by mass.

From the viewpoint of enzyme activity, an extraction solvent preferably contains a reducing agent such as dithiothreitol or β-mercaptoethanol. The reducing agent is preferably dithiothreitol. The concentration of dithiothreitol in an extraction solvent is preferably from 0.1 mM to 1M and more preferably from 1 mM to 10 mM. In a case that dithiothreitol is present in an extraction solvent, a structure such as a disulfide bond in the enzyme is easily to be retained and enzyme activity is easily to be enhanced.

From the viewpoint of enzyme activity, the extraction solvent preferably contains chelating agent such as ethylenediaminetetraacetic acid (EDTA). The concentration of EDTA in the extraction solvent is preferably from 0.01 mM to 1 M and more preferably from 0.1 mM to 10 mM. In a case that EDTA is present in the extraction solvent, a metal ion which may reduce enzyme activity is chelated, and therefore, enzyme activity is easily to be enhanced.

The extraction solvent may contain, besides the ingredients described above, a known ingredient which can be added to an enzyme extraction solvent.

The mutated tetraprenyl-β-curcumene cyclase may be used singly, or in combination of two or more kinds thereof.

The conditions of a reaction between the mutated tetraprenyl-β-curcumene cyclase and squalene are not particularly restricted as long as the conditions are such that an enzyme reaction can be proceeded. For example, the reaction temperature and the reaction time may be appropriately selected based on the activity of the mutated tetraprenyl-β-curcumene cyclase or the like. From the viewpoint of reaction efficiency, the reaction temperature and the reaction time may be, for example, from 4° C. to 100° C. and from 1 hour to 30 days, and preferably 30° C. to 60° C. and 16 hours to 20 days. From the viewpoint of reaction efficiency, the pH is, for example, from 3 to 10, and preferably from 6 to 8.

A reaction solvent is not particularly restricted as long as the reaction solvent does not inhibit an enzyme reaction, and a buffer or the like which is usually used can be used. For example, the same solvent as an extraction solvent which is used in a step of extracting an enzyme can be used. An extraction liquid (for example, cell-free extract) containing the mutated tetraprenyl-β-curcumene cyclase may be used as it is as an enzyme liquid in the reaction.

From the viewpoint of reaction efficiency, the concentration ratio between mutated tetraprenyl-β-curcumene cyclase and squalene which is the substrate thereof in a production reaction of ambrein is preferably from 1 to 10000, more preferably from 10 to 5000, still more preferably from 100 to 3000, and still further preferably from 1000 to 2000 in terms of the molar concentration ratio (substrate/enzyme) of the substrate to the enzyme.

From the viewpoint of reaction efficiency, the concentration of squalene to be used for an enzyme reaction is preferably from 0.000001% by mass to 10% by mass, and more preferably from 0.00001% by mass to 1% by mass with respect to the total mass of the reaction solvent.

The reaction step between the mutated tetraprenyl-β-curcumene cyclase and squalene may be repeated a plurality of times. This can increase the yield of ambrein. In the case that a plurality of reaction steps are repeated, the purification method may be comprised: a step of recharging squalene to be the substrate; a step of recovering and purifying a reaction product in a reaction liquid after inactivating the enzyme by a known method; and the like. In a case that squalene is recharged, a charging point in time, and the amount of charging of squalene can be appropriately set according to the concentration of the mutated tetraprenyl-β-curcumene cyclase in the reaction liquid, the amount of the substrate remained in the reaction liquid, or the like.

According to another embodiment of the preparation method of the present invention, it is characterized by culturing the microorganism or the transformant of the present invention.

An ambrein can be prepared by culturing the microorganism or the host cell transformed with the expression vector. Regarding the yeast, the yeast may be cultured in a conventional YPD medium and the like. For example, the yeast wherein a gene is introduced by a homologous recombination, or the yeast having the expression vector, is precultured. Then, the precultured yeast is inoculated to an YPD medium or the like, and it is cultured for about 24 to 240 hours, preferably about 72 to 120 hours. The ambrein which is secreted into the medium can be used as is, or after a purification by the known method. In particular, as the purification method, there may be mentioned solvent extraction, recrystallization, distillation, column chromatography, and HPLC.

<<Function>>

A mechanism by which squalene is converted to monocyclic 3-deoxyachilleol A in the monocyclic pathway and a mechanism by which 8 in the monocyclic pat 17,21-triene is converted to ambrein in the bicyclic pathway by the mutated tetraprenyl-β-curcumene cyclase of the present invention, has not been analyzed in detail, but are estimated as follows. However, the present invention is by no means limited to the following explanation.

As mentioned above, the mutated tetraprenyl-β-curcumene cyclase of the present invention has QXXXGX(W/F) motif (motif A), QXXXX(G/A)X(F/W/Y) motif (motif B), QXXXGX(F/W/Y) motif (motif C), QXXXGXW motif (motif D), and QXXXGX(F/W) motif (motif E). In the mutated TC of the present invention, a mutated DXDD motif in which the 4th aspartic acid of the DXDD motif is substituted with an amino acid other than aspartic acid (preferably cysteine or glycine), interacts with the motifs A to E which are widely present in the tetraprenyl-β-curcumene cyclase, and whereby it is considered that the enzyme activity is exerted stably.

While, the mutated tetraprenyl-β-curcumene cyclase of the present invention does not have QXXXGXW motif possessed by squalene-hopene cyclase. The squalene-hopene cyclase also has the motifs A to E. However, even when the DXDD motif is converted to the mutated DXDD motif, the effect of the present invention can't be obtained. Thus, it is considered that the QXXXGXW motif possessed by the squalene-hopene cyclase inhibits the enzyme activity obtained in the present invention.

EXAMPLES

The present invention now will be further illustrated by, but is by no means limited to, the following Examples.

Example 1

In this Example, the mutated tetraprenyl-β-curcumene cyclase gene was cloned and an expression vector was constructed.

The mutated tetraprenyl-β-curcumene cyclase gene was introduced into a pCold-TF vector (NdeI-XhoI site).

A polynucleotide encoding wild type tetraprenyl-β-curcumene cyclase was obtained by PCR using *Bacillus megaterium* chromosomal DNA as a template. The polynucleotide was inserted into the NdeI-XhoI site of pCold-TF vector. Using the obtained vector as a template, a site-specific mutation was introduced thereinto by a Quick Change method so that aspartic acid at position 373 is substituted with cysteine, to obtain the expression vector containing the mutated tetraprenyl-β-curcumene cyclase gene.

Then, a transformant of *Escherichia coli* BL21 (DE3) was prepared using the obtained expression vector containing the mutated tetraprenyl-β-curcumene cyclase gene.

Example 2

In this Example, an enzyme activity of the mutated tetraprenyl-β-curcumene cyclase was examined using squalene, 3-deoxyachilleol A, or 8α-hydroxypolypoda-13,17,21-triene as a substrate.

The transformant prepared in Example 1 was inoculated in the LB medium (1 L) containing ampicillin (50 mg/L) and the whole was cultivated at 37° C., for 3 hours while shaking. After cultivation, isopropyl-β-thiogalactopyranoside (IPTG: 0.1M) was added thereto, the whole was shaken at 15° C., for 24 hours, to induce the expression of the mutated tetraprenyl-β-curcumene cyclase.

Thereafter, the bacterial cells collected by centrifugation (6,000×g, 10 minutes) were washed with 50 mM Tris-HCl buffer (pH 7.5), and then, suspended in 30 mL of buffer A [containing 50 mM Tris-HCl buffer (pH 7.5), 0.1 v/v % Triton X-100, 2.5 mM dithiothreitol, 1 mM EDTA]. Further, the suspension of bacterial cells were sonicated at 4° C., for 20 minutes, using UP2005 sonicator (Hielscher Ultrasonics, Teltow, Germany). The sonicated sample was centrifuged at 12,300×g, for 20 minutes, and the supernatant obtained after centrifugation was used as a cell-free extract solution A.

Squalene (250 μg) was mixed with Triton X-100 (5 mg) for solubilization and then added to buffer A (1 mL) to prepare a squalene solution. The whole amount of the squalene solution was added to cell-free extract A (4 mL) to prepare a reaction solution and incubated at 30° C., for 64 hours. The molar ratio (substrate/enzyme) of squalene (substrate) to the mutated tetraprenyl-β-curcumene cyclase (enzyme) in the reaction solution was about 200.

After the incubation, methanol (6 mL) was added to the reaction solution to stop the enzymatic reaction, and then, n-hexane (5 mL) was added to the reaction solution, and the reaction product was extracted three times.

The resulting extract was applied to a silica gel column chromatography (solvent; n-hexane:ethyl acetate=100:20 (volume ratio)) to obtain a fraction of n-hexane:ethyl acetate=100:20. The fraction was concentrated. The analysis result by GC/MS is shown in FIG. 3.

Figure 3:
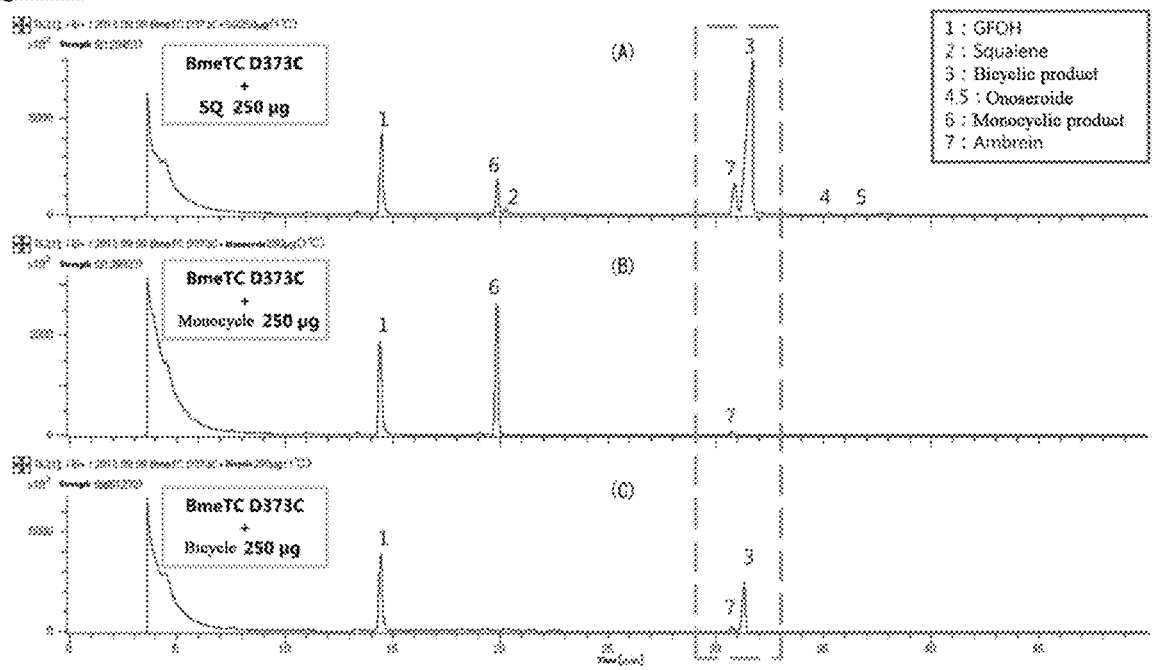
FIG. 3 are charts showing products obtained by reacting the mutated tetraprenyl-β-curcumene cyclase of the present invention with squalene (A), 3-deoxyachilleol A (B), or bicyclic triterpene (C) which are used as substrates.

(In FIG. 3, the term "BmeTC D373C" means an enzyme wherein the amino acid, aspartic acid (D), at position 373 of the tetraprenyl-β-curcumene cyclase derived from *Bacillus megaterium* is substituted with cysteine (C). In addition, the term "SQ" means "squalene", the terms "monocycle" and "monocyclic product" means "3-deoxyachilleol A" and the terms "bicycle", and "bicyclic product" means "8α-hydroxypolypoda-13,17,21-triene." Hereinafter, the same applies to the other figures.)

The mutated tetraprenyl-β-curcumene cyclase was reacted with squalene to obtain ambrein. Further, 3-deoxyachilleol A and 8α-hydroxypolypoda-13,17,21-triene were also produced. Therefore, it is considered that ambrein was generated through the monocyclic pathway (a) and (b) and the bicyclic pathway (c) and (d) shown in FIG. 2, by using the mutated tetraprenyl-β-curcumene cyclase. Further, the mutated tetraprenyl-β-curcumene cyclase was reacted with squalene to obtain ambrein, and the mutated tetraprenyl-β-curcumene cyclase was reacted with 8α-hydroxypolypoda-13,17,21-triene to obtain ambrein. These results support that the mutated tetraprenyl-β-curcumene cyclase generates ambrein by the monocyclic pathway and the bicyclic pathway.

Example 3

The procedure described in Example 2 was repeated, except that the reaction solution was incubated at 30° C., for 5 days, instead of incubating at 30° C., for 64 hours to prepare ambrein.

Figure 4:
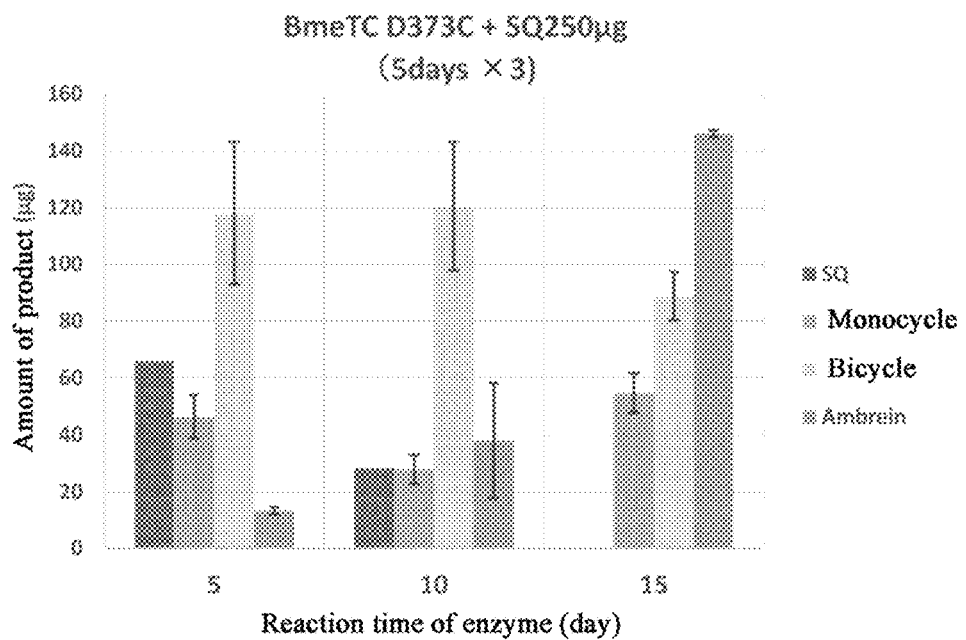
FIG. 4 is a graph showing timeline of the production amounts of 3-deoxyachilleol A, bicyclic triterpene, and ambrein after 5 days, 10 days, and 15 days, in the case that the mutated tetraprenyl-β-curcumene cyclase of the present invention reacts with squalene as a substrate.
Figure 5:
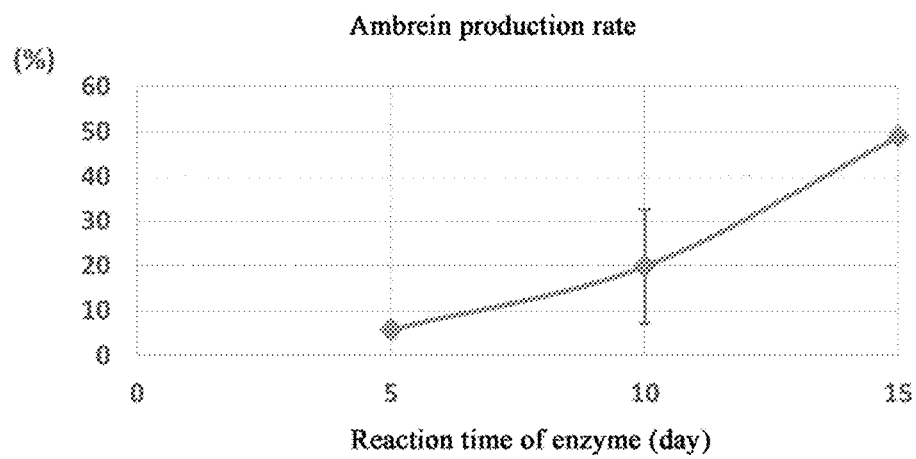
FIG. 5 is a graph showing an ambrein production rate which is increasing in proportion to the increase in the enzyme reaction time, in the case that the mutated tetraprenyl-portion to the incr of the present invention reacts with squalene.

FIG. 4 shows the product amounts of squalene, ambrein, 3-deoxyachilleol A, and 8α-hydroxypolypoda-13,17,21-triene after 5 days, 10 days and 15 days. It is considered that squalene was converted to 3-deoxyachilleol A and 8α-hydroxypolypoda-13,17,21-triene, and further converted to ambrein, according to a time course. After 5 days of enzymatic reaction, the production rate of ambrein relative to squalene was 8%, as shown in FIG. 5. After 10 days of enzymatic reaction, the production rate of ambrein relative to squalene increased to 20%. After 15 days of enzymatic reaction, the production rate of ambrein relative to squalene was further increased to 50%.

According to the mutated tetraprenyl-β-curcumene cyclase of the present invention, ambrein can be synthesized in one step using squalene as a substrate, without a concomitant use of a mutated squalene-hopene cyclase.

Comparative Example 1

The procedures described in Examples 1 to 3 were repeated, except that a tetraprenyl-β-curcumene cyclase gene without mutation was used instead of the mutated tetraprenyl-β-curcumene cyclase gene, and whether or not the tetraprenyl-β-curcumene cyclase gene without mutation can generate ambrein from squalene was examined.

Figure 6:
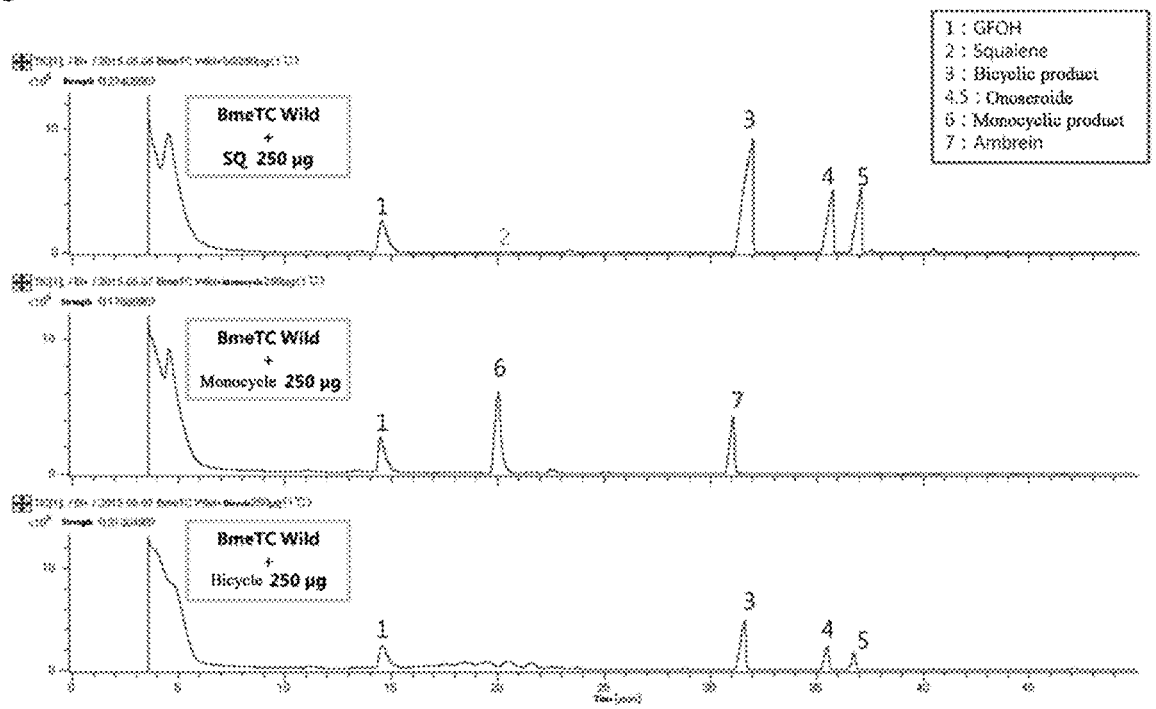
FIG. 6 are charts showing products obtained by reacting the wild type tetraprenyl-β-curcumene cyclase with squalene.

As a result, ambrein was able to be generated only when the tetraprenyl-β-curcumene cyclase was reacted with 3-deoxyachilleol A, as shown in FIG. 6, and it was impossible to synthesize ambrein using squalene as a substrate.

Example 4

In this Example, an HMGR gene and the mutated tetraprenyl-β-curcumene cyclase gene were cloned in order to obtain a transformant expressing the HMGR and a mutated tetraprenyl-β-curcumene cyclase in yeast.

The HMGR gene was obtained from an ML-236B resistant strain which is obtained by culturing the yeast (*Saccharomycopsis fibuligera*) using a medium containing ML-236B (SEQ ID NO. 4; Hereinafter, the HMGR gene obtained from the ML-236B resistant strain is sometimes referred to as "ADK4653" or "ADK4653 gene".).

(1) Cloning of Mutated HMGR (tHMGR) Gene (Truncating Type) and Construction of Expression Vector Using the genomic DNA of the ML-236B resistant strain as a template, the mutated HMGR gene (truncating type, nucleotide sequence 1540 to 3066 of SEQ ID NO: 4) was amplified by PCR using the primers shown in SEQ ID NOS: 5 and 6.

The PCR product was analyzed by an agarose gel electrophoresis and inserted into an expression vector pAUR123 (Takara Bio Inc.), to obtain an expression vector for the truncated HMGR (hereinafter sometimes referred to as "ADK 4653_tHMGR") of the ML-236B resistant strain.

(2) Cloning of Mutated Tetraprenyl-β-Curcumene Cyclase Gene

The wild-type tetraprenyl-β-curcumene cyclase gene was synthesized by optimizing codons for budding yeast (*Saccharomyces cerevisiae*) based on the amino acid sequence of the enzyme. The synthesized gene was inserted into the cloning site (restriction enzyme EcoRV site) of the vector pUCF (FASMAC). Next, amino acid substitution mutation was introduced into the wild type tetraprenyl-β-curcumene cyclase gene. Specifically, the mutated tetraprenyl-β-curcumene cyclase gene having a substitution from aspartic acid to cysteine at amino acid position 373 of the wild type tetraprenyl-β-curcumene cyclase was obtained.

Using PrimeSTAR DNA Polymerase (Takara Bio Inc.), the mutation-introduced vector was prepared using mutagenic primers shown in SEQ ID NOs: 7 and 8, according to the instruction manual.

(3) Construction of Expression Vector

For constructing an expression vector, the shuttle vector (pAUR123, Takara Bio) for protein expression obtained by cloning the truncated HMGR (tHMGR) gene in Example 4 (1) was used.

First, an expression cassette consisting of the phosphoglycerate kinase gene (PGK1) promoter derived from the budding yeast (*Saccharomyces cerevisiae*) and the CYC1 terminator was inserted between the 6982nd position and the 1st position in the nucleotide sequence of the vector pAUR123. Next, using the vector as a template, an expression vector fragment containing a mutated HMGR (tHMGR) gene was prepared by PCR using the primers shown in SEQ ID NOs: 9 and 10.

Further, using the vector obtained in Example 4 (2) as a template, the mutated tetraprenyl-β-curcumene cyclase gene fragment was prepared using the primers shown in SEQ ID NOs: 11 and 12, in the same manner.

The PCR product was analyzed by an agarose gel electrophoresis. Then it was subjected to a restriction enzyme (DPNI) treatment, and purified using a NucleoSpin Gel and PCR Clean-up column (MACHEREY-NAGEL). The target gene was cloned into the vector prepared in Example 4 (3) according to the user's manual using the In-Fusion HD Cloning Kit (Clontech). The resulting reaction solution was directly used for transformation of *Escherichia coli* competent cells (HST 08, Takara Bio Inc.). Regarding the positive clones, it was confirmed that the target gene was introduced by colony PCR, to obtain an expression vector.

Example 5

In this Example, a yeast transformant was obtained using the vector obtained in Example 4 (3). Production of squalene, ambrein, monocyclic compound (3-deoxyachilleol A) or bicyclic compound (8α-Hydroxypolypoda-13,17,21-triene) was examined using the transformant.

(1) Transformation of Yeast

Sake yeast (*Saccharomyces cerevisiae*, Kyokai 701) was transformed with the expression vector obtained in Example 4(3). The vector was preliminarily digested with a restriction enzyme (EcoO65I (BstEII, BstPI), Takara Bio Inc.) at one site within the resistance marker gene, and it was introduced by homologous recombination using the linearized vector. The yeast was transformed in accordance with a conventional lithium acetate method using Frozen-EZ Yeast Transformation II (ZYMO RESARCH Inc.). Regarding the resulting clones, it was confirmed that the target gene was introduced by colony PCR.

(2) Production of Squalene, Ambrein, Monocyclic Compound (3-Deoxyachilleol A) or Bicyclic Compound (8α-Hydroxypolypoda-13,17,21-Triene) by Yeast Transformant (Culture of Yeast Transformant)

The truncated ADK4653 gene was constitutively expressed by the alcohol dehydrogenase 1 gene promoter (ADH1), and the mutated tetraprenyl-β-curcumene cyclase gene was constitutively expressed by the phosphoglycerate kinase gene promoter (PGK1). It was confirmed that a mevalonate pathway was enhanced by overexpression of the ADK4653 gene introduced by transformation, in addition to the HMGR gene originally possessed by sake yeast, by measuring squalene which is a metabolite of the pathway. Further, it was also examined whether or not ambrein, monocyclic compound (3-deoxyachilleol A) or bicyclic compound (8a-Hydroxypolypoda-13,17,21-triene) that is not originally produced by sake yeast, was produced.

The yeast transformant was inoculated with 0.5 mL of the culture liquid which was pre-cultured for 24 hours in a YPD medium, in 50 mL of the YPD medium (glucose concentration of 5%) using a conical flask (500 mL volume) with baffle and incubated at 28° C., 250 rpm. The sample was collected after 5 days and squalene, ambrein, monocyclic compound (3-deoxyachilleol A) or bicyclic compound (8a-Hydroxypolypoda-13,17,21-triene) accumulated in the cells was analyzed.

Comparative Example 2

In this Comparative Example, the truncated ADK4653 gene and the wild-type tetraprenyl-β-curcumene cyclase gene were cloned. The vector of the tetraprenyl-β-curcumene cyclase gene was constructed in the same manner as in Example 4 (3) using the wild-type gene before mutation was introduced.

Comparative Example 3

In this Comparative Example, a yeast transformant was obtained using the vector obtained in Comparative Example 2. Production of squalene, ambrein, monocyclic compound (3-deoxyachilleol A) or bicyclic compound (8a-Hydroxypolypoda-13,17,21-triene) was examined using the transformant. (1) Transformation of yeast and (2) production of squalene, ambrein, monocyclic compound or bicyclic compound by yeast transformant were carried out in the same manner as in Example 5.

(Analysis of Products)

The cells obtained in Example 5 and Comparative Example 3 were disrupted and extracted using hexane, to prepare samples. 3 mL of the culture liquids were centrifuged to remove the supernatant, and then 1.5 ml of zirconia beads (YTZ ball, φ 0.5 mm, Nikkato) were added to the cells, and one minute of pulverization (3200 rpm/min) with a bead crusher (Taitec, uT-12) was repeated 5 times. 1.5 mL of hexane was added to the disrupted liquids, and the whole was stirred for 1 minute with the bead crusher for three times, so as to extract. Then, the organic layer was collected after centrifugation (16000 rpm/min). The resulting extracts were dried and solidified under nitrogen gas flow, and redissolved in 400 µL of hexane for GC analysis. GC analysis was carried out using a gas chromatograph GC-2014 (Shimadzu Corporation), HP 5 capillary column (30 m×0.32 mm×0.25 µm, Agilent Technologies), and FID as a detector. The analysis conditions were as follows: SPL temperature 300° C., FID temperature 320° C., split ratio 30.0, total flow rate 25.0 mL/min, linear velocity 19.3 cm/sec, column temperature 220 to 300° C. (rate of temperature increase 1° C./min), and at 300° C. for a 10 min hold.

Figure 7:
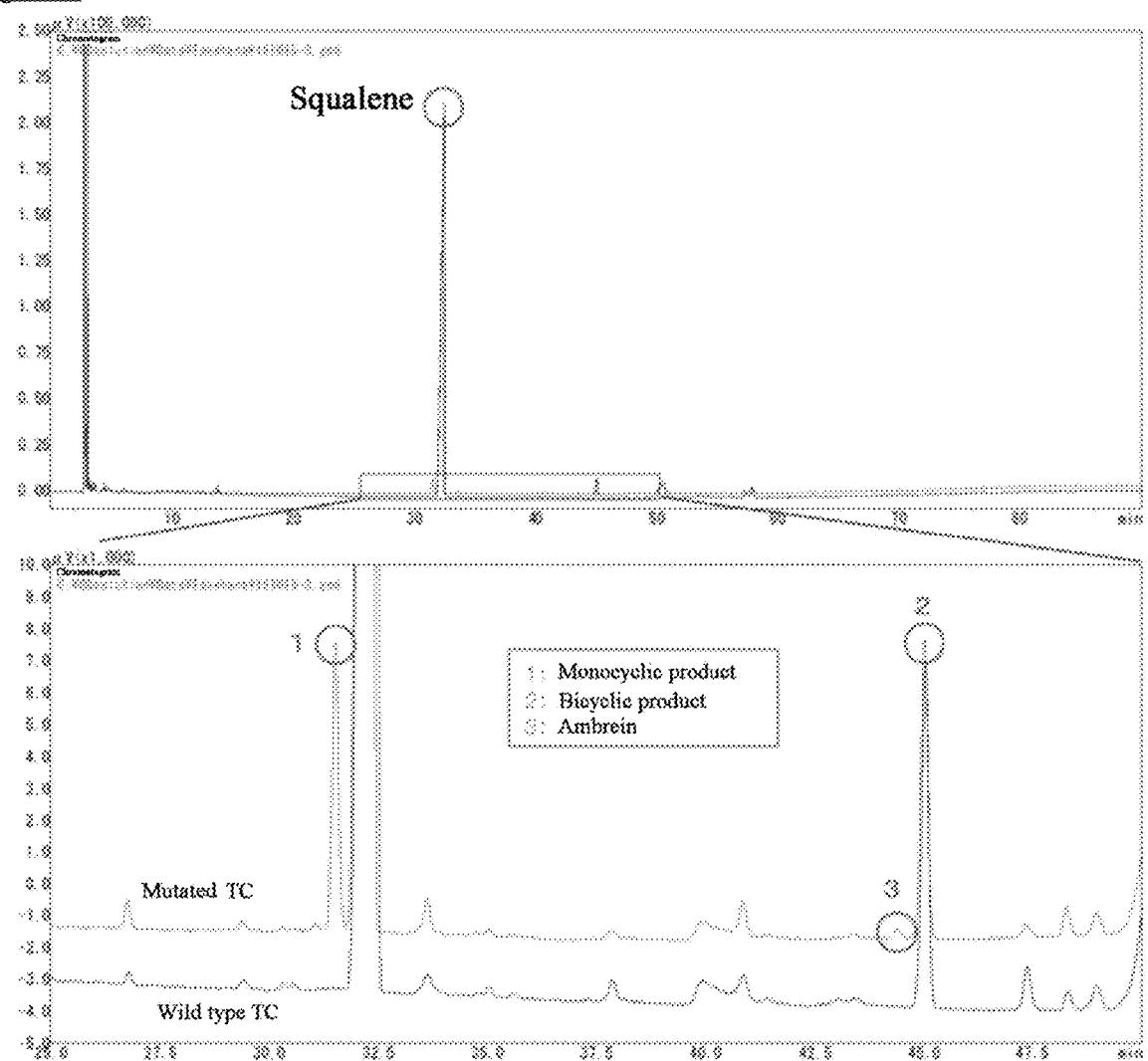
FIG. 7 are charts showing a chromatogram obtained by analyzing a product of a yeast transformant containing mutated tetraprenyl-β-curcumene cyclase by gas chromatography. The mutated TC means yeast in which the mutated tetraprenylβ-curcumene cyclase (D373C) gene is expressed, and the wild type TC means yeast in which the wild type tetraprenyl-e wild type the wie of a yeast traThe "monocyclic product" is "3-deoxyachilleol A" and the "bicyclic product" is "8α-hydroxypolypoda-13,17,21-triene."

The analysis results by gas chromatography are shown in FIG. 7. Squalene, ambrein, monocyclic compound (3-deoxyachilleol A) and bicyclic compound (8a-Hydroxypolypoda-13,17,21-triene) were detected from the host in which the mutated HMGR gene and the mutated tetraprenyl-β-curcumene cyclase gene were simultaneously expressed, obtained in Examples 4 and 5 (FIG. 7)

Sake yeast expressing the mutated HMGR gene (truncated form) showed a remarkable increase in the production of squalene. It was confirmed that the mevalonate pathway which is strictly controlled in nature as the rate-limiting step in metabolism can be enhanced. Further, it was confirmed that ambrein, monocyclic compound (3-deoxyachilleol A) or bicyclic compound (8a-Hydroxypolypoda-13,17,21-triene) which was not originally produced in Sake yeast can be produced by coexpression of the mutated tetraprenyl-β-curcumene cyclase gene. That is to say, this result shows that molecular breeding of hosts coexpressing the mutated HMGR gene and mutated tetraprenyl-β-curcumene cyclase gene enables the ambrein production in yeast.

On the other hand, in the host obtained in Comparative Examples 2 and 3, in which the mutated HMGR gene and the wild type tetraprenyl-β-curcumene cyclase gene were simultaneously expressed, squalene and the bicyclic compound (8a-Hydroxypolypoda-13,17,21-triene) were detected. Sake yeast expressing a mutant HMGR gene (truncated form) showed a remarkable increase in the production of squalene and it was confirmed that the mevalonate pathway can be enhanced. Further, it was confirmed that bicyclic compound (8a-Hydroxypolypoda-13, 17,21-triene) which was not originally produced in Sake yeast can be produced by coexpression of the wild type tetraprenyl-β-curcumene cyclase gene. However, ambrein, or monocyclic compound (3-deoxyachilleol A) was not detected, and it was confirmed that they were not produced. That is to say, this result shows that even when the wild type tetraprenyl-β-curcumene cyclase gene was expressed, ambrein was not produced in yeast.

In addition, it is known that the production amount of the compound downstream of the mevalonate pathway, particularly squalene, increases dramatically, by expressing the mutated HMGR gene (truncated form) having a specific amino acid sequence in yeast as an HMGR (hydroxymethylglutaryl CoA reductase) which is one of the enzymes in the mevalonate pathway. Therefore, co-expression of the mutated HMGR gene (truncated form) and wild type tetraprenyl-β-curcumene cyclase gene enables the ambrein production in yeast.

Example 6

In this Example, the mutated tetraprenyl-β-curcumene cyclase derived from *Bacillus subtilis* was prepared to produce ambrein. The amino acid identity of the tetraprenyl-β-curcumene cyclase between *Bacillus subtilis* and *Bacillus megaterium* is 50%.

The mutated tetraprenyl-β-curcumene cyclase gene was synthesized based on the amino acid sequence of tetraprenyl-β-curcumene cyclase from *Bacillus subtilis* (GenBank accession number: AB 618206). The gene was designed so that aspartic acid, the fourth amino acid of the DXDD motif, was substituted with cysteine. The gene optimized for expression in *E. coli* was synthesized and inserted into the NdeI-XhoI site of the pCold-TF vector. A transformant of *Escherichia coli* BL21 (DE3) was prepared with the resulting expression vector containing the mutated tetraprenyl-β-curcumene cyclase gene.

Then, a cell-free extract solution containing the mutated tetraprenyl-β-curcumene cyclase was obtained in the same manner as in Example 2.

Subsequently, squalene (50 µg) was mixed with Tween-80 (1 mg) for solubilization, and then the mixture was added to a buffer B [50 mM Tris-HCl buffer (pH 7.5), 0.1 v/v % Tween-80, 0.1 w/v % sodium ascorbate, 2.5 mM dithiothreitol, 1 mM EDTA] (1 mL) to prepare a squalene solution liquid. The whole amount of the squalene liquid was added to the cell-free extract (4 mL) to prepare a reaction liquid and the reaction liquid was incubated at 30° C. for 64 hours. The molar ratio (substrate/enzyme) between squalene (substrate) and the mutated tetraprenyl-β-curcumene cyclase (enzyme) in the reaction liquid was about 1000.

After the incubation, methanol (6 mL) containing 15 mass % of potassium hydroxide was added to the reaction liquid to stop the enzymatic reaction, and then n-hexane (5 mL) was added to the reaction liquid and the reaction product was extracted three times.

The resulting extract was applied to a silica gel column chromatography (solvent; n-hexane:ethyl acetate=100:20 (volume ratio)) to obtain a fraction of n-hexane:ethyl acetate=100:20. The fraction was concentrated, and an analysis by gas chromatography mass spectrometer (GC-MS) was performed to confirm that ambrein was produced.

INDUSTRIAL APPLICABILITY

According to the present invention, in the production of ambrein, it is possible to produce ambrein in one step using squalene as a substrate by using the mutated tetraprenyl-β-curcumene cyclase. Ambrein obtained by the present invention can be used, for example, as a raw material for production of pharmaceuticals and the like.

Although the present invention has been described with reference to specific embodiments, various changes and modifications obvious to those skilled in the art are possible without departing from the scope of the appended claims.

The invention claimed is:

1. A mutated tetraprenyl-β-curcumene cyclase, comprising a polypeptide wherein the polypeptide comprises
   90% or more sequence identity with an amino acid sequence of SEQ ID NO: 1 wherein aspartic acid at position 373 from an N-terminal in said amino acid sequence of SEQ ID NO: 1 is substituted with cysteine or glycine, or 90% or more sequence identity with an amino acid sequence of SEQ ID NO: 13 wherein aspartic acid at position 378 from an N-terminal in said amino acid sequence of SEQ ID NO: 13 is substituted with cysteine or glycine, and
   wherein the polypeptide exhibits ambrein production activity using squalene as a substrate.

2. The mutated tetraprenyl-β-curcumene cyclase according to claim 1, comprising the amino acid sequence of SEQ ID NO: 1, wherein aspartic acid at position 373 from the N-terminal is substituted with cysteine or glycine, or the amino acid sequence of SEQ ID NO: 13, wherein aspartic acid at position 378 from the N-terminal is substituted with cysteine or glycine.

3. A polynucleotide encoding the mutated tetraprenyl-β-curcumene cyclase according to claim 1.

4. A microorganism comprising the polynucleotide according to claim 3.

5. The microorganism according to claim 4, further comprising a polynucleotide encoding hydroxymethylglutaryl CoA reductase.

6. A vector comprising a DNA having the polynucleotide according to claim 3.

7. A cell transformed with the vector according to claim 6.

8. The cell according to claim 7, further comprising a vector comprising a DNA having a polynucleotide encoding hydroxymethylglutaryl CoA reductase.

9. A method for preparing ambrein comprising bringing into contact the mutated tetraprenyl-β-curcumene cyclase according to claim 1 with squalene, to obtain ambrein.

10. A method for preparing ambrein comprising culturing the microorganism according to claim 4.

11. The mutated tetraprenyl-β-curcumene cyclase of claim 1, comprising the amino acid sequence of SEQ ID NO: 1, wherein aspartic acid at position 373 from the N-terminal is substituted with cysteine or glycine.

12. A mutated tetraprenyl-β-curcumene cyclase of claim 1, comprising the amino acid sequence of SEQ ID NO: 13, wherein aspartic acid at position 378 from the N-terminal is substituted with cysteine or glycine.

13. A method for preparing ambrein characterized by bringing into contact the mutated tetraprenyl-β-curcumene cyclase according to claim 1 with 8a-hydroxypolypoda-13,17,21-triene, to obtain ambrein.

14. A method for preparing 3-deoxyachilleol A characterized by bringing into contact the mutated tetraprenyl-β-curcumene cyclase according to claim 1 with squalene, to obtain 3-deoxyachilleol A.

15. A mutated tetraprenyl-β-curcumene cyclase, comprising amino acid sequence SEQ ID NO: 17 wherein aspartic acid at position 340 from an N-terminal in said amino acid sequence of SEQ ID NO: 17 is substituted with cysteine or glycine.

16. The mutated tetraprenyl-β-curcumene cyclase of claim 15, wherein the polypeptide exhibits ambrein production activity using squalene as a substrate.

* * * * *

SEQUENCE LISTING

```
<160> NUMBER OF SEQ ID NOS: 18

<210> SEQ ID NO 1
<211> LENGTH: 625
<212> TYPE: PRT
<213> ORGANISM: Bacillus megaterium
<220> FEATURE:
<221> NAME/KEY: misc_feature
<222> LOCATION: (1)..(7)
<223> OTHER INFORMATION: Xaa can be any naturally occurring amino acid

<400> SEQUENCE: 1

Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175
```

-continued

```
Val Ala Gly Asn Lys Lys Phe Ser Leu Thr Ser Arg His Thr Pro Ser
            180                 185                 190

Leu Ser His Leu Asp Val Arg Glu Gln Lys Gln Glu Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
    290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Asp Thr Ser Ala Ala Ile Arg Ala Leu Ser Arg Arg
    370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
        435                 440                 445

Leu Glu Cys Leu Gly Asn Phe Ala Gly Met Asn Lys Ser His Pro Ser
    450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
        515                 520                 525

Gly Phe Gly Glu Ser Cys Tyr Ser Ala Ser Leu Lys Lys Tyr Val Pro
    530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
                565                 570                 575

Phe Leu Leu Asn Pro Asn Leu Thr Glu Gln Gln Thr His Tyr Pro Thr
            580                 585                 590

Gly Ile Gly Leu Pro Gly Gln Phe Tyr Ile Gln Tyr His Ser Tyr Asn
```

```
            595                 600                 605
Asp Ile Phe Pro Leu Leu Ala Leu Ala His Tyr Ala Lys Lys His Ser
    610                 615                 620

Ser
625

<210> SEQ ID NO 2
<211> LENGTH: 1878
<212> TYPE: DNA
<213> ORGANISM: Bacillus megaterium
<220> FEATURE:
<221> NAME/KEY: misc_feature
<222> LOCATION: (1)..(17)
<223> OTHER INFORMATION: n is a, c, g, or t

<400> SEQUENCE: 2
atgatcatat tgctaaagga agttcagcta gagattcagc gaagaatcgc ctatctgcgc      60
ccaacacaaa aaaatgacgg gtcatttcgc tactgttttg aaacaggcgt tatgcctgat     120 gcgttttaa ttatgcttct tcgcaccttt gatttagata agaagtgtt gattaaacaa       180 ttaaccgaac ggatcgtttc ccttcaaaat gaagatggtc tttggacgtt gtttgatgat    240
gaagaacata acttatctgc cactattcaa gcttatacag ctcttttata ttcaggatat    300
taccaaaaaa acgaccggat tttgcgaaaa gcagaaagat atattataga ttcaggaggc    360
atttcgcgcg ctcattttct cacaagatgg atgcttctg ttaacggtct atacgagtgg     420
ccaaagctat tttacctccc gctttctctt ttgctcgtgc ctacctatgt accgcttaac    480
ttttatgaat taagcactta tgccagaatt cacttcgttc cgatgatggt agcaggaaac    540 aaaaaattt cacttacttc taggcataca ccttctcttt ctcatttaga tgtaagagaa     600
cagaaacagg aatcggagga aactactcaa gaatcacgcg cttcaatttt tctagtcgac    660
catttaaaac agctggcttc tttaccttct tacatccaca aacttggtta tcaagcagcc    720
gagcgttaca tgctagaaag aattgaaaaa gatggaacac tctacagcta cgccaccctct   780 actttttta tgatttacgg tcttttggct cttggctata aaaagattc atttgtgatc      840 caaaaagcaa ttgacgggat tgttcacta cttagtacat gcagcggcca cgtgcacgta    900
gaaaactcca cgtcaaccgt tgggatacc cgctgctct cttacgctct acaggaagca    960
ggtgtaccgc agcaagatcc catgattaaa ggcacaactc gctacttaaa gaaaagacag   1020
catacaaagc ttggagattg gcagtttcat aacccaaata cagcacctgg aggctggggg   1080
ttttccgata ttaatacaaa taaccctgac ttagactgta cgtctgctgc atcagagct    1140 ctttctagaa gagcgcaaac cgatacagat tatttggagt cttggcaaag agggattaac   1200
tggctgctgt ccatgcaaaa caagatggg ggttttgctg catttgaaaa aaataccgac    1260
tctattttat ttacttatct gccgcttgaa atgcaaaag atgcagcgac ggatccggct    1320
actgccgatt taaccggtcg agtgcttgag tgtctcggaa actttgctgg tatgaataaa   1380
tcccaccctt cgattaaagc tgcagtaaaa tggctgtttg atcatcaatt ggataacggg   1440
agctggtacg gccggtgggg agtttgctat atttacggaa cgtgggccgc tattacagga   1500
ctccgtgctg taggggtttc tgcttctgat ccgcgtatca tcaaagctat caactggctc   1560
aaaagcattc aacaagaaga cggtggattc ggagaatcat gctatagcgc ttctttaaaa   1620
aaatatgtgc cactatcgtt tagcacccc tctcaaacgg cttgggctct cgatgcttta    1680
atgacaatat gtccgttaaa agatcaatcc gttgaaaaag gaattaaatt tttactaaat   1740
ccaaatctta cagagcagca aactcattac cccacgggaa ttggtcttcc tggacaattt   1800
```

-continued

```
tatattcagt accacagcta caatgatatt tttcctcttc ttgcacttgc ccactacgca    1860
aaaaaacatt cttcgtaa                                                  1878
```

<210> SEQ ID NO 3
<211> LENGTH: 1022
<212> TYPE: PRT
<213> ORGANISM: Saccharomycopsis fibuligera

<400> SEQUENCE: 3

```
Met Phe Ser Leu Ser Asn Tyr Val Ser Asn Trp Leu Ala Ser Leu Ala
1               5                   10                  15

Arg Leu Ser Ala His Lys Pro Ile His Val Ile Phe Leu Thr Thr Leu
            20                  25                  30

Leu Thr Ala Val Ala Tyr Leu Ser Val Val Asp Glu Tyr Leu Asn Phe
        35                  40                  45

Asp Ser Phe Asp Ile Ser Asn Val Ser Phe Tyr His Pro Pro Ser Ser
    50                  55                  60

Lys Asp Tyr Lys Asp Trp Thr Leu Ile Glu Asp Ala Ser Ala Tyr Pro
65                  70                  75                  80

Asn Ala Ala Arg Ile Ala Ile Thr Pro Leu Glu Phe Arg Arg Ile Ala
                85                  90                  95

Lys His Glu Ile Pro Ala Ile Ala Asn Thr Phe Tyr Gly Val Asp Ser
            100                 105                 110

Thr Glu Lys Tyr Leu Ile Ser Glu Tyr Glu Asn Ala Gln Asp Ser Ile
        115                 120                 125

Asp Ser Ile Arg Thr Val Val Ser Asn Asp Gly Thr Ala Trp Lys Ile
    130                 135                 140

Val His Gln Tyr Lys Thr Ser Lys Tyr Gln Glu Tyr Leu Lys Asn Ala
145                 150                 155                 160

Tyr Lys Thr Leu Gln Ser Val Ile Arg Gly Ala Glu Thr Tyr Asp Ile
                165                 170                 175

Ala Ile Ile Thr Ile Ala Tyr Ala Ala Met Tyr Tyr Thr Phe Phe Lys
            180                 185                 190

Leu Phe Tyr Asp Met Arg Thr Gln Ala Asn Ser Lys Phe Trp Leu Gly
        195                 200                 205

Phe Ala Ser Ala Ser Ser Leu Phe Ala Phe Leu Leu Ala Val Gly
    210                 215                 220

Thr Ala Lys Ile Phe Asn Ile Arg Val Ser Leu Ser Leu Ser Glu
225                 230                 235                 240

Gly Ile Pro Phe Leu Val Ala Thr Val Gly Phe Asn Arg Ile Val Lys
                245                 250                 255

Leu Ser Ala Ala Val Leu Asn Ala Ala Val Asp Lys Glu Ser His
            260                 265                 270

Ser Ile Ser Leu Leu Ile Tyr Arg Gln Leu Lys Asp Lys Ala Leu Asn
        275                 280                 285

Phe Val Lys Asp Gln Leu Leu Cys Ala Ala Ala Phe Val Gly Cys Ser
    290                 295                 300

Ile Tyr Ala Ser His Leu Glu Gly Leu Arg Ser Phe Cys Leu Leu Ser
305                 310                 315                 320

Ala Phe Ile Met Ile Tyr Asp Val Leu Leu Thr Tyr Ser Tyr Tyr Ser
                325                 330                 335

Ala Val Leu Ala Leu Lys Val Glu Ile Asn Met Ile His Gln Ser Ile
            340                 345                 350
```

-continued

Ala Leu Lys Asp Ala Leu Glu Glu Asp Gly Ile Pro Glu Leu Ala Ala
            355                 360                 365
Arg Gln Ala Ser Leu Ala Ser Phe Gly Ser Gln Lys Glu Leu Ser Leu
        370                 375                 380
Gly Pro Asn Ser Gly Tyr Val Thr Ala Phe Lys Ile Ala Ser Val Ala
385                 390                 395                 400
Phe Phe Phe Ala Phe His Ala Tyr Leu Val Gly Ser Asn Trp Val Phe
                405                 410                 415
Leu Ser Ser Asn Glu Asp Ile Ile Glu Gly His Asn Leu Ser Lys Ser
            420                 425                 430
Ile Ala Lys His Ile Ser Ile Gly Ser Thr Gly Thr Val Val Thr Leu
        435                 440                 445
Leu Glu Pro Lys Ile Tyr Val Pro Lys Asn Ile Leu Phe Gln Val Glu
    450                 455                 460
Asp Leu Val Ile Ser Ile Leu Glu Lys Leu Ser Thr Ala Ile Arg Asp
465                 470                 475                 480
Lys Phe Ile Ser Lys Thr Leu Leu Phe Phe Leu Gly Thr Ser Ser Ala
                485                 490                 495
Ile Asn Val Tyr Leu Leu Asn Ala Ala Arg Ala His Ser Ile Asp Lys
            500                 505                 510
Pro Ser Gln Arg Leu Ser Lys Ala Ile Ala Ser Lys Glu Ala Ser Arg
        515                 520                 525
Arg Ala Lys Ala Ala Tyr Glu Ser Gln Lys Ser Val Ser Lys Ser Thr
    530                 535                 540
Asp Asp Thr Ala Ser Ser Glu Pro Thr Phe Asp Val Lys Asn Ile Leu
545                 550                 555                 560
Pro Asn Ser Gly Ile Glu His Thr Phe Glu Glu Leu Val Asp Ile Leu
                565                 570                 575
Lys Asn Gly Glu Val Ser Ser Leu Ser Asn Glu Glu Val Thr Thr Leu
            580                 585                 590
Val Val Lys Asp Lys Leu Pro Leu Tyr Ala Leu Glu Lys Lys Leu Gly
        595                 600                 605
Asp Thr Thr Arg Ala Val Ala Val Arg Arg Gln Ala Ile Ser Lys Leu
    610                 615                 620
Ala Lys Ser Pro Ile Val Asp Ser Ser Val Pro Tyr Leu Asn Tyr
625                 630                 635                 640
Asp Tyr Asp Lys Val Phe Gly Ala Cys Cys Glu Asn Val Ile Gly Tyr
                645                 650                 655
Ile Pro Leu Pro Leu Gly Val Ala Gly Pro Leu Leu Ile Asp Gly Lys
            660                 665                 670
Pro Phe His Ile Pro Met Ala Thr Thr Glu Gly Cys Leu Val Ala Ser
        675                 680                 685
Thr Met Arg Gly Cys Lys Ala Ile Asn Ala Gly Gly Gly Val Ser Thr
    690                 695                 700
Val Leu Thr Arg Asp Gly Met Thr Arg Gly Pro Cys Val Lys Phe Pro
705                 710                 715                 720
Ser Leu Gln Arg Ala Gly Ala Cys Lys Ile Trp Leu Asp Ser Glu Glu
                725                 730                 735
Gly Gln Asn Leu Leu Lys Lys Ser Phe Asn Ser Thr Ser Arg Phe Ala
            740                 745                 750
Arg Leu Gln His Val Gln Thr Ala Ile Ala Gly Ser Leu Leu Phe Ile
        755                 760                 765
Arg Phe Arg Thr Thr Thr Gly Asp Ala Met Gly Met Asn Met Ile Ser

```
                770               775               780
Lys Gly Val Glu Phe Thr Leu Lys Gln Met Val Glu Glu Tyr Gly Trp
785               790               795               800

Ser Asp Met Asp Val Ile Ser Val Ser Gly Asn Tyr Cys Thr Asp Lys
              805               810               815

Lys Ala Ala Ser Ile Asn Trp Thr Asn Gly Arg Gly Lys Ser Ile Val
              820               825               830

Ala Glu Ala Arg Ile Pro Gly Glu Val Val Arg Lys Val Leu Lys Ser
              835               840               845

Asp Val Asp Ala Leu Val Glu Leu Asn Val Ser Lys Asn Leu Ile Gly
              850               855               860

Ser Ala Met Ala Gly Ser Ile Gly Gly Phe Asn Ala His Ala Ala Asn
865               870               875               880

Leu Val Thr Ala Val Phe Leu Ala Cys Gly Gln Asp Pro Ala Gln Asn
              885               890               895

Val Glu Ser Ser Asn Cys Ile Thr Leu Ile Asp Asn Val Asp Gly Asp
              900               905               910

Leu Gln Ile Ser Val Ser Met Pro Ser Ile Glu Val Gly Thr Ile Gly
              915               920               925

Gly Gly Thr Ile Leu Glu Pro Gln Gly Ala Met Leu Asp Leu Leu Gly
930               935               940

Val Arg Gly Pro His Pro Thr Thr Pro Gly Ala Asn Ala His Gln Leu
945               950               955               960

Ala Lys Val Val Ala Ser Ala Val Leu Ala Ala Glu Leu Ser Leu Cys
              965               970               975

Ser Ala Leu Ala Ala Gly His Leu Val Gln Ser His Met Gln His Asn
              980               985               990

Arg Gly Lys Pro Ala Ala Pro Ala  Ala Ala Pro Ser Ser  Lys Ala Asp
              995               1000              1005

Val Gln  Arg Leu Thr Asp Gly  Ser Lys Ile Cys Ile  Lys Ser
   1010              1015              1020

<210> SEQ ID NO 4
<211> LENGTH: 3069
<212> TYPE: DNA
<213> ORGANISM: Saccharomycopsis fibuligera

<400> SEQUENCE: 4
atgtttagcc ttagtaatta tgtgtccaat tggctcgcgt cattggcaag gttgtcggca      60
cacaaaccaa tccacgttat attcttaaca acgttgttaa ccgctgttgc ttacttgtct     120
gtcgtcgacg agtatctcaa ctttgactca ttcgatatct ccaatgtttc cttctatcat     180
cctccatctt caaggactata aagattgg actttaattg aggatgctag tgcttatcca     240
aacgcagctc gtattgcaat cactccactt gagtttagaa gaattgctaa acatgaaatc     300
ccggctatag caaacacttt ttacggcgtc gactccaccg agaaatactt gatttctgag     360
tacgaaaatg cccaggacag cattgactca atcagaactg ttgtttccaa tgatgggact     420
gcttggaaga ttgttcacca gtacaagacc agcaaatatc aagaatacct caaaaatgct     480
tacaaaacct acagtctgt  tattcgtggt gctgaaactg atgatattgc tatcattaca     540
attgcctacg ctgccatgta ctacacccttt ttaagctct tttatgatat gagaacccaa     600
gccaactcca agttctggtt gggttttgct tcagcctcat catctctgtt tgcattttg     660
cttgctgttg gaactgccaa aatctttaat attagagttt ccttattgag cttgtctgaa     720
```

```
ggcattccat ttttggttgc cacggttgga ttcaacagaa ttgtaaagct ttccgccgct      780
gttttgaacg ccgctgcagt tgacaaagag tctcatagta tcagtttatt gatttataga      840
caacttaagg ataaagccct caattttgtc aaagatcaat tgttatgtgc tgctgcattt      900
gttgggtgct caatttatgc atcgcacttg aaggattga gaagcttttg tttattgagt      960
gcattcatca tgatttacga cgtgcttttg acttattcct actattctgc tgtcttggct     1020
cttaaagttg aaatcaacat gattcaccaa tctattgctc ttaaggatgc attagaagaa     1080
gacggtattc ctgaacttgc tgctagacaa gcttctttgg catcatttgg gtcacaaaaa     1140
gaacttagct tgggtccaaa cagcggatat gttaccgcat tcaaaattgc tagcgttgca     1200
tttttcttcg cattccatgc ttacttagtg ggcagtaact gggttttctt gagcagcaat     1260
gaggacatta tcgaaggcca caacttgtcc aagtcgattg ctaaacatat ttctattgga     1320
tcaaccggta ctgttgtcac tttattggaa ccgaaaattt acgttccaaa gaacatttta     1380
tttcaagttg aagatcttgt tatcagtatt cttgaaaaat tgtctactgc tatcagagat     1440
aaatttatta gtaagacttt gcttttcttt ttgggtacca gttctgccat caatgtctac     1500
ttgttgaacg ctgctagagc ccactccatt gataagccat ctcaacgtct tagcaaggct     1560
attgcttcaa agaagcatc tagaagagca aaagctgctt atgaatcaca aaagagtgtt     1620
tcaaagagca ccgatgatac tgctagtagc gagccaactt ttgacgtaaa gaatatattg     1680
ccaaatagtg tgattgaaca tacttttgaa gaattagttg acattctcaa gaatggcgaa     1740
gtttctagct tgtctaatga agaagttact acccttgttg ttaaagataa attgccatta     1800
tatgctcttg aaaagaagtt aggtgacact actcgtgctg ttgctgttcg tcgtcaagct     1860
atttccaaat tggccaaaag cccaattgtt gatagctcta gtgttccata cttgaattac     1920
gattatgata aggtgtttgg cgcatgttgt gaaaacgtca ttggttatat tccattgcct     1980
cttggtgttg ctggtccatt gttaattgat ggtaagccat tccatattcc aatggctact     2040
actgaaggtt gtcttgttgc ttctaccatg cgcggttgta aagctattaa tgctggtggc     2100
ggtgttagca ccgtcttgac tagagatggt atgacaagag gtccttgtgt taaattccca     2160
tctttgcaac gtgccggtgc ttgtaagatt tggttagatt ctgaagaagg tcaaaacttg     2220
ttgaaaaaat cattcaattc tacttctaga tttgctagat tgcaacatgt tcaaactgcc     2280
attgctggtt ctttgctttt cattagattt agaactacta ctggtgatgc tatgggtatg     2340
aatatgattt ccaaaggtgt tgaatttaca ttgaaacaaa tggttgaaga atatggttgg     2400
tctgatatgg atgttatctc tgtttccggt aactactgta ctgataagaa agccgcttct     2460
attaactgga ccaatggtcg tggtaagagt attgttgctg aagctcgtat tcctggagaa     2520
gttgtcagaa aagttcttaa gagtgacgtt gatgctcttg ttgaattaaa cgtcagcaag     2580
aatttgattg gttctgcaat ggccggctct attggtggtt caatgctca tgctgcaaat     2640 ttggtcactg ctgttttctt agcctgcggt caagatcctg ctcaaaatgt tgaaagttcc     2700
aactgtatca ctttaattga taatgttgat ggcgatttgc aaatatccgt ttctatgcca     2760
tctattgaag ttggtactat tggtggtggt actattcttg aacctcaagg tgctatgctt     2820
gatttattgg gagttcgtgg tccacatcca actactccag gggctaatgc tcatcagctt     2880
gcaaaggttg ttgcttctgc tgttttggcc gctgaattat cattgtgttc agcattggct     2940
gctggtcatt tagttcaaag tcatatgcaa cataaccgtg gtaaacctgc tgctccagcg     3000
gccgctccat caagcaaggc tgatgttcag cgtttgactg atggatcaaa gatctgtatc     3060
aaatcttaa                                                             3069
```

<210> SEQ ID NO 5
<211> LENGTH: 45
<212> TYPE: DNA
<213> ORGANISM: Artificial Sequence
<220> FEATURE:
<223> OTHER INFORMATION: tHGMR primer-1

<400> SEQUENCE: 5
aatcaactgg tacccgggat gtctcaacgt cttagcaagg ctatt                45

<210> SEQ ID NO 6
<211> LENGTH: 44
<212> TYPE: DNA
<213> ORGANISM: Artificial Sequence
<220> FEATURE:
<223> OTHER INFORMATION: tHGMR primer-1

<400> SEQUENCE: 6
ttagttaacc tctagagctc ttaagatttg atacagatct tga                  44

<210> SEQ ID NO 7
<211> LENGTH: 27
<212> TYPE: DNA
<213> ORGANISM: Artificial Sequence
<220> FEATURE:
<223> OTHER INFORMATION: TC mut ptimer-1

<400> SEQUENCE: 7
ctggattgta cttctgccgc cataagg                                    27

<210> SEQ ID NO 8
<211> LENGTH: 27
<212> TYPE: DNA
<213> ORGANISM: Artificial Sequence
<220> FEATURE:
<223> OTHER INFORMATION: TC mut primer-2

<400> SEQUENCE: 8
agaagtacaa tccagatcag gattatt                                    27

<210> SEQ ID NO 9
<211> LENGTH: 20
<212> TYPE: DNA
<213> ORGANISM: Artificial Sequence
<220> FEATURE:
<223> OTHER INFORMATION: tHMGR frag primer-1

<400> SEQUENCE: 9
tcgacatgga acagaagttg                                            20

<210> SEQ ID NO 10
<211> LENGTH: 22
<212> TYPE: DNA
<213> ORGANISM: Artificial Sequence
<220> FEATURE:
<223> OTHER INFORMATION: tHMGR frag primer-2

<400> SEQUENCE: 10
gatccttgtt ttatatttgt tg                                         22

<210> SEQ ID NO 11
<211> LENGTH: 37
<212> TYPE: DNA
<213> ORGANISM: Artificial Sequence
<220> FEATURE:

<223> OTHER INFORMATION: TC frag primer-1

<400> SEQUENCE: 11
tataaaacaa ggatccatga ttatcctatt gaaggag                          37

<210> SEQ ID NO 12
<211> LENGTH: 37
<212> TYPE: DNA
<213> ORGANISM: Artificial Sequence
<220> FEATURE:
<223> OTHER INFORMATION: TC frag primer-2

<400> SEQUENCE: 12
tctgttccat gtcgacttat gaggaatgct tctttgc                          37

<210> SEQ ID NO 13
<211> LENGTH: 632
<212> TYPE: PRT
<213> ORGANISM: Bacillus subtilis

<400> SEQUENCE: 13

```
Met Gly Thr Leu Gln Glu Lys Val Arg Arg Tyr Gln Lys Lys Thr Ile
1               5                   10                  15

Ala Glu Leu Lys Asn Arg Gln Asn Ala Asp Gly Ser Trp Thr Phe Cys
                20                  25                  30

Phe Glu Gly Pro Ile Met Thr Asn Ser Phe Phe Ile Leu Leu Leu Thr
            35                  40                  45

Ser Leu Asp Glu Gly Glu Asn Glu Lys Glu Leu Ile Ser Ala Leu Ala
        50                  55                  60

Ala Gly Ile Arg Glu Lys Gln Gln Pro Asp Gly Thr Phe Ile Asn Tyr
65                  70                  75                  80

Pro Asp Glu Thr Ser Gly Asn Ile Thr Ala Thr Val Gln Gly Tyr Val
                85                  90                  95

Gly Met Leu Ala Ser Gly Cys Phe His Arg Ser Asp Pro His Met Arg
            100                 105                 110

Lys Ala Glu Gln Ser Ile Ile Ser His Gly Gly Leu Arg His Val His
        115                 120                 125

Phe Met Thr Lys Trp Met Leu Ala Val Asn Gly Leu Tyr Pro Trp Pro
130                 135                 140

Val Leu Tyr Leu Pro Leu Ser Leu Met Ala Leu Pro Pro Thr Leu Pro
145                 150                 155                 160

Val His Phe Tyr Gln Phe Ser Ala Tyr Ala Arg Ile His Phe Ala Pro
                165                 170                 175

Met Ala Val Thr Leu Asn Gln Arg Phe Val Leu Lys Asn Arg Asn Ile
            180                 185                 190

Pro Ser Leu Arg His Leu Asp Pro His Met Thr Lys Asn Pro Phe Thr
        195                 200                 205

Trp Leu Arg Ser Asp Ala Phe Glu Glu Arg Asp Leu Thr Ser Ile Trp
    210                 215                 220

Ser His Trp Asn Arg Ile Phe His Ala Pro Phe Ala Phe Gln Gln Leu
225                 230                 235                 240

Gly Leu Gln Thr Ala Lys Thr Tyr Met Leu Asp Arg Ile Glu Lys Asp
                245                 250                 255

Gly Thr Leu Tyr Ser Tyr Ala Ser Ala Thr Ile Phe Met Val Tyr Ser
            260                 265                 270

Leu Leu Ser Leu Gly Val Ser Arg Tyr Ser Pro Val Ile Lys Arg Ala
        275                 280                 285
```

Ile Asn Gly Ile Lys Ser Leu Met Thr Lys Cys Asn Gly Ile Pro Tyr
290                 295                 300

Leu Glu Asn Ser Thr Ser Thr Val Trp Asp Thr Ala Leu Ile Ser Tyr
305                 310                 315                 320

Ala Leu Gln Lys Asn Gly Val Thr Glu Thr Asp Gly Ser Ile Thr Lys
            325                 330                 335

Ala Ala Ala Tyr Leu Leu Glu Arg Gln His Thr Lys Arg Ala Asp Trp
            340                 345                 350

Ser Val Lys Asn Pro Ser Ala Ala Pro Gly Gly Trp Gly Phe Ser Asn
            355                 360                 365

Ile Asn Thr Asn Asn Pro Asp Cys Asp Asp Thr Ala Ala Val Leu Lys
            370                 375                 380

Ala Ile Pro His Ser Tyr Ser Pro Ser Ala Trp Glu Arg Gly Val Ser
385                 390                 395                 400

Trp Leu Leu Ser Met Gln Asn Asn Asp Gly Gly Phe Ser Ala Phe Glu
                405                 410                 415

Lys Asn Val Asn His Pro Leu Ile Arg Leu Leu Pro Leu Glu Ser Ala
                420                 425                 430

Glu Asp Ala Ala Val Asp Pro Ser Thr Ala Asp Leu Thr Gly Arg Val
            435                 440                 445

Leu His Phe Leu Gly Glu Lys Ala Gly Phe Thr Glu Lys His Gln His
450                 455                 460

Ile Gln Arg Ala Val Asn Trp Leu Phe Glu His Gln Glu Gln Asn Gly
465                 470                 475                 480

Ser Trp Tyr Gly Arg Trp Gly Val Cys Tyr Ile Tyr Gly Thr Trp Ala
                485                 490                 495

Ala Leu Thr Gly Met His Ala Cys Glu Val Asp Arg Lys His Pro Ala
            500                 505                 510

Ile Gln Lys Ala Leu Arg Trp Leu Lys Ser Ile Gln His Asp Asp Gly
            515                 520                 525

Ser Trp Gly Glu Ser Cys Asn Ser Ala Glu Val Lys Thr Tyr Val Pro
            530                 535                 540

Leu His Lys Gly Thr Ile Val Gln Thr Ala Trp Ala Leu Asp Ala Leu
545                 550                 555                 560

Leu Thr Tyr Glu Ser Ser Glu His Pro Ser Val Val Lys Gly Met Gln
                565                 570                 575

Tyr Leu Thr Asp Ser Ser Tyr His Gly Ala Asp Ser Leu Ala Tyr Pro
            580                 585                 590

Ala Gly Ile Gly Leu Pro Lys Gln Phe Tyr Ile Arg Tyr His Ser Tyr
            595                 600                 605

Pro Tyr Val Phe Ser Leu Leu Ala Val Gly Lys Tyr Leu Asn Ser Ile
610                 615                 620

Glu Lys Glu Thr Ala Asn Glu Thr
625                 630

<210> SEQ ID NO 14
<211> LENGTH: 1899
<212> TYPE: DNA
<213> ORGANISM: Bacillus subtilis

<400> SEQUENCE: 14
atgggcaccc tgcaggagaa agtgcgtcgc tatcagaaga aaactatcgc cgaactgaag        60
aaccgccaga acgccgatgg tagctggacc ttctgcttcg aaggcccgat catgacaaat       120

-continued

```
agttttttca ttctgctgct gaccagtctg gacgaaggtg agaacgagaa ggaactgatt    180
agcgcactgg ccgcaggtat ccgcgagaag cagcagccgg acggcacatt tattaactac    240
ccggacgaaa ccagcggcaa tatcaccgcc accgtgcagg gctatgttgg catgctggcc    300
agtggctgct tcaccgcag tgatccgcac atgcgcaaag ccgaacagag catcattagc    360
catggcggcc tgcgccatgt gcattttatg acaaaatgga tgctggccgt gaatggtctg    420
tatccgtggc ctgttctgta cttaccgctg agcttaatgg ccctgccgcc gacactgccg    480
gtgcactttt atcagttcag cgcctacgcc cgtattcact cgcccctat ggccgtgacc     540 ctgaatcaac gcttcgtgtt aaaaaaccgt aatattccga gtctgcgcca tctggacccg    600
cacatgacaa agaacccgtt cacctggctg cgcagcgacg ccttcgaaga cgcgacctg    660 accagcattt ggagccactg gaatcgtatc tttcacgcac cgttcgcatt ccagcagctg    720
ggcctgcaga ccgccaaaac ctatatgctg gaccgcattg aaaaggacgg caccctgtac    780
agctatgcca gcgcaaccat cttcatggtg tatagcctgc tgagcctggg tgttagtcgc    840
tacagcccgg ttatcaaacg cgcaattaat ggcattaaaa gtctgatgac caagtgcaac    900
ggtatcccgt atctggagaa tagcacaagc accgtttggg ataccgccct gatcagctat    960
gccctgcaga agaatggcgt taccgaaacc gacggcagca ttaccaaagc cgccgcctat   1020
ctgctggagc gccagcatac caaacgcgca gactggagcg tgaagaatcc tagtgccgca   1080
cctggcggct ggggtttcag taacatcaac accaataacc cggactgcga ttgtaccgca   1140
gcagtgttaa aggccattcc gcatagttat agcccgagcg catgggagcg cggtgttagc   1200
tggctgctga gtatgcagaa caatgatggc ggcttcagcg ccttcgaaaa gaacgtgaat   1260
catccgctga tccgcctgct gccgctggag agtgcagaag atgccgcagt ggatccgagc   1320
accgcagatc tgaccggccg cgtgttacac tttctgggtg aaaaggcagg cttcaccgag   1380
aaacaccagc atatccagcg cgcagtgaat tggctgtttg agcaccagga gcagaatggt   1440
agttggtacg gccgctgggg cgtttgttat atctacggta cctgggccgc cctgaccggc   1500
atgcacgcct gcgaagtgga tcgcaaacat ccggccattc agaaagccct gcgctggctg   1560
aaaagcattc agcatgacga tggcagctgg ggtgaaagct gcaacagtgc cgaggtgaag   1620
acctatgttc cgctgcacaa gggcaccatc gtgcagacag catgggccct ggacgccctg   1680
ctgacctacg aaagcagtga gcatcctagc gtggtgaagg gcatgcagta cctgacagac   1740
agtagctatc acggtgccga cagtttagcc tacccggcag gcattggcct gccgaagcag   1800
ttttacatcc gttaccacag ctacccgtac gtgtttagcc tgctggcagt gggcaagtac   1860
ctgaacagca tcgaaaagga gacagccaac gagacctaa                          1899
```

<210> SEQ ID NO 15
<211> LENGTH: 625
<212> TYPE: PRT
<213> ORGANISM: Bacillus megaterium

<400> SEQUENCE: 15

```
Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
            20                  25                  30

Phe Glu Thr Gly Val Met Pro Asp Ala Phe Leu Ile Met Leu Leu Arg
        35                  40                  45

Thr Phe Asp Leu Asp Lys Glu Val Leu Ile Lys Gln Leu Thr Glu Arg
    50                  55                  60
```

-continued

```
Ile Val Ser Leu Gln Asn Glu Asp Gly Leu Trp Thr Leu Phe Asp Asp
 65                  70                  75                  80

Glu Glu His Asn Leu Ser Ala Thr Ile Gln Ala Tyr Thr Ala Leu Leu
             85                  90                  95

Tyr Ser Gly Tyr Tyr Gln Lys Asn Asp Arg Ile Leu Arg Lys Ala Glu
                100                 105                 110

Arg Tyr Ile Ile Asp Ser Gly Gly Ile Ser Arg Ala His Phe Leu Thr
            115                 120                 125

Arg Trp Met Leu Ser Val Asn Gly Leu Tyr Glu Trp Pro Lys Leu Phe
        130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Ser Glu Glu Thr
        195                 200                 205

Thr Gln Glu Ser Arg Ala Ser Ile Phe Leu Val Asp His Leu Lys Gln
210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
290                 295                 300

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
                325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
        355                 360                 365

Pro Asp Leu Asp Cys Thr Ser Ala Ala Ile Arg Ala Leu Ser Arg Arg
370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
            420                 425                 430

Lys Asp Ala Ala Thr Asp Pro Ala Thr Ala Asp Leu Thr Gly Arg Val
        435                 440                 445

Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480
```

```
Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
            500                 505                 510

Ile Ile Lys Ala Ile Asn Trp Leu Lys Ser Ile Gln Gln Glu Asp Gly
            515                 520                 525

Gly Phe Gly Glu Ser Cys Tyr Ser Ala Ser Leu Lys Lys Tyr Val Pro
            530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Gln Ser Val Glu Lys Gly Ile Lys
            565                 570                 575

Phe Leu Leu Asn Pro Asn Leu Thr Glu Gln Gln Thr His Tyr Pro Thr
            580                 585                 590

Gly Ile Gly Leu Pro Gly Gln Phe Tyr Ile Gln Tyr His Ser Tyr Asn
            595                 600                 605

Asp Ile Phe Pro Leu Leu Ala Leu Ala His Tyr Ala Lys Lys His Ser
610                 615                 620

Ser
625

<210> SEQ ID NO 16
<211> LENGTH: 632
<212> TYPE: PRT
<213> ORGANISM: Bacillus subtilis

<400> SEQUENCE: 16

Met Gly Thr Leu Gln Glu Lys Val Arg Arg Tyr Gln Lys Lys Thr Ile
1               5                   10                  15

Ala Glu Leu Lys Asn Arg Gln Asn Ala Asp Gly Ser Trp Thr Phe Cys
                20                  25                  30

Phe Glu Gly Pro Ile Met Thr Asn Ser Phe Phe Ile Leu Leu Leu Thr
            35                  40                  45

Ser Leu Asp Glu Gly Glu Asn Glu Lys Glu Leu Ile Ser Ala Leu Ala
    50                  55                  60

Ala Gly Ile Arg Glu Lys Gln Gln Pro Asp Gly Thr Phe Ile Asn Tyr
65                  70                  75                  80

Pro Asp Glu Thr Ser Gly Asn Ile Thr Ala Thr Val Gln Gly Tyr Val
                85                  90                  95

Gly Met Leu Ala Ser Gly Cys Phe His Arg Ser Asp Pro His Met Arg
            100                 105                 110

Lys Ala Glu Gln Ser Ile Ile Ser His Gly Gly Leu Arg His Val His
            115                 120                 125

Phe Met Thr Lys Trp Met Leu Ala Val Asn Gly Leu Tyr Pro Trp Pro
            130                 135                 140

Val Leu Tyr Leu Pro Leu Ser Leu Met Ala Leu Pro Pro Thr Leu Pro
145                 150                 155                 160

Val His Phe Tyr Gln Phe Ser Ala Tyr Ala Arg Ile His Phe Ala Pro
                165                 170                 175

Met Ala Val Thr Leu Asn Gln Arg Phe Val Leu Lys Asn Arg Asn Ile
            180                 185                 190

Pro Ser Leu Arg His Leu Asp Pro His Met Thr Lys Asn Pro Phe Thr
            195                 200                 205

Trp Leu Arg Ser Asp Ala Phe Glu Glu Arg Asp Leu Ser Ile Trp
            210                 215                 220
```

```
Ser His Trp Asn Arg Ile Phe His Ala Pro Phe Ala Phe Gln Gln Leu
225                 230                 235                 240

Gly Leu Gln Thr Ala Lys Thr Tyr Met Leu Asp Arg Ile Glu Lys Asp
            245                 250                 255

Gly Thr Leu Tyr Ser Tyr Ala Ser Ala Thr Ile Phe Met Val Tyr Ser
        260                 265                 270

Leu Leu Ser Leu Gly Val Ser Arg Tyr Ser Pro Val Ile Lys Arg Ala
        275                 280                 285

Ile Asn Gly Ile Lys Ser Leu Met Thr Lys Cys Asn Gly Ile Pro Tyr
    290                 295                 300

Leu Glu Asn Ser Thr Ser Thr Val Trp Asp Thr Ala Leu Ile Ser Tyr
305                 310                 315                 320

Ala Leu Gln Lys Asn Gly Val Thr Glu Thr Asp Gly Ser Ile Thr Lys
            325                 330                 335

Ala Ala Ala Tyr Leu Leu Glu Arg Gln His Thr Lys Arg Ala Asp Trp
        340                 345                 350

Ser Val Lys Asn Pro Ser Ala Ala Pro Gly Gly Trp Gly Phe Ser Asn
        355                 360                 365

Ile Asn Thr Asn Asn Pro Asp Cys Asp Cys Thr Ala Ala Val Leu Lys
    370                 375                 380

Ala Ile Pro His Ser Tyr Ser Pro Ser Ala Trp Glu Arg Gly Val Ser
385                 390                 395                 400

Trp Leu Leu Ser Met Gln Asn Asn Asp Gly Gly Phe Ser Ala Phe Glu
            405                 410                 415

Lys Asn Val Asn His Pro Leu Ile Arg Leu Leu Pro Leu Glu Ser Ala
        420                 425                 430

Glu Asp Ala Ala Val Asp Pro Ser Thr Ala Asp Leu Thr Gly Arg Val
        435                 440                 445

Leu His Phe Leu Gly Glu Lys Ala Gly Phe Thr Glu Lys His Gln His
    450                 455                 460

Ile Gln Arg Ala Val Asn Trp Leu Phe Glu His Gln Glu Gln Asn Gly
465                 470                 475                 480

Ser Trp Tyr Gly Arg Trp Gly Val Cys Tyr Ile Tyr Gly Thr Trp Ala
            485                 490                 495

Ala Leu Thr Gly Met His Ala Cys Glu Val Asp Arg Lys His Pro Ala
        500                 505                 510

Ile Gln Lys Ala Leu Arg Trp Leu Lys Ser Ile Gln His Asp Asp Gly
        515                 520                 525

Ser Trp Gly Glu Ser Cys Asn Ser Ala Glu Val Lys Thr Tyr Val Pro
    530                 535                 540

Leu His Lys Gly Thr Ile Val Gln Thr Ala Trp Ala Leu Asp Ala Leu
545                 550                 555                 560

Leu Thr Tyr Glu Ser Ser Glu His Pro Ser Val Val Lys Gly Met Gln
            565                 570                 575

Tyr Leu Thr Asp Ser Ser Tyr His Gly Ala Asp Ser Leu Ala Tyr Pro
        580                 585                 590

Ala Gly Ile Gly Leu Pro Lys Gln Phe Tyr Ile Arg Tyr His Ser Tyr
        595                 600                 605

Pro Tyr Val Phe Ser Leu Leu Ala Val Gly Lys Tyr Leu Asn Ser Ile
    610                 615                 620

Glu Lys Glu Thr Ala Asn Glu Thr
625                 630
```

<210> SEQ ID NO 17
<211> LENGTH: 592
<212> TYPE: PRT
<213> ORGANISM: Bacillus licheniformis

<400> SEQUENCE: 17

Met Thr Asp Ser Phe Phe Ile Leu Met Leu Thr Ser Leu Gly Asp Gln
1               5                   10                  15

Asp Ser Ser Leu Ile Ala Ser Leu Ala Glu Arg Ile Arg Ser Arg Gln
            20                  25                  30

Ser Glu Asp Gly Ala Phe Arg Asn His Pro Asp Glu Arg Ala Gly Asn
        35                  40                  45

Leu Thr Ala Thr Val Gln Gly Tyr Thr Gly Met Leu Ala Ser Gly Leu
    50                  55                  60

Tyr Asp Arg Lys Ala Pro His Met Gln Lys Ala Glu Ala Phe Ile Lys
65                  70                  75                  80

Asp Ala Gly Gly Leu Lys Gly Val His Phe Met Thr Lys Trp Met Leu
                85                  90                  95

Ala Ala Asn Gly Leu Tyr Pro Trp Pro Arg Ala Tyr Ile Pro Leu Ser
            100                 105                 110

Phe Leu Leu Ile Pro Ser Tyr Phe Pro Leu His Phe Tyr His Phe Ser
        115                 120                 125

Thr Tyr Ala Arg Ile His Phe Val Pro Met Ala Ile Thr Phe Asn Arg
    130                 135                 140

Arg Phe Ser Leu Lys Asn Asn Gln Ile Gly Ser Leu Arg His Leu Asp
145                 150                 155                 160

Glu Ala Met Ser Lys Asn Pro Leu Glu Trp Leu Asn Ile Arg Ala Phe
                165                 170                 175

Asp Glu Arg Thr Phe Tyr Ser Phe Asn Leu Gln Trp Lys Gln Leu Phe
            180                 185                 190

Gln Trp Pro Ala Tyr Val His Gln Leu Gly Phe Glu Ala Gly Lys Lys
        195                 200                 205

Tyr Met Leu Asp Arg Ile Glu Glu Asp Gly Thr Leu Tyr Ser Tyr Ala
    210                 215                 220

Ser Ala Thr Met Phe Met Ile Tyr Ser Leu Leu Ala Met Gly Ile Ser
225                 230                 235                 240

Lys Asn Ala Pro Val Val Lys Lys Ala Val Ser Gly Ile Lys Ser Leu
                245                 250                 255

Ile Ser Ser Cys Gly Lys Glu Gly Ala His Leu Glu Asn Ser Thr Ser
            260                 265                 270

Thr Val Trp Asp Thr Ala Leu Ile Ser Tyr Ala Met Gln Glu Ser Gly
        275                 280                 285

Val Pro Glu Gln His Ser Ser Thr Ser Ser Ala Ala Asp Tyr Leu Leu
    290                 295                 300

Lys Arg Gln His Val Lys Lys Ala Asp Trp Ala Val Ser Asn Pro Gln
305                 310                 315                 320

Ala Val Pro Gly Gly Trp Gly Phe Ser His Ile Asn Thr Asn Asn Pro
                325                 330                 335

Asp Leu Asp Asp Thr Ala Ala Leu Lys Ala Ile Pro Phe Gln Arg
            340                 345                 350

Arg Pro Asp Ala Trp Asn Arg Gly Leu Ala Trp Leu Leu Ser Met Gln
        355                 360                 365

Asn Lys Asp Gly Gly Phe Ala Ala Phe Glu Lys Asp Val Asp His Pro
    370                 375                 380

-continued

Leu Ile Arg Asn Leu Pro Leu Glu Ser Ala Ala Glu Ala Ala Val Asp
385                 390                 395                 400

Pro Ser Thr Ala Asp Leu Thr Gly Arg Val Leu His Leu Leu Gly Leu
                405                 410                 415

Lys Gly Arg Phe Thr Asp Asn His Pro Ala Val Arg Arg Ala Leu Arg
                420                 425                 430

Trp Leu Asp His His Gln Lys Ala Asp Gly Ser Trp Tyr Gly Arg Trp
                435                 440                 445

Gly Val Cys Phe Ile Tyr Gly Thr Trp Ala Ala Leu Thr Gly Met Lys
                450                 455                 460

Ala Val Gly Val Ser Ala Asn Gln Thr Ser Val Lys Lys Ala Ile Ser
465                 470                 475                 480

Trp Leu Lys Ser Ile Gln Arg Glu Asp Gly Ser Trp Gly Glu Ser Cys
                485                 490                 495

Lys Ser Cys Glu Ala Lys Arg Phe Val Pro Leu His Phe Gly Thr Val
                500                 505                 510

Val Gln Ser Ser Trp Ala Leu Glu Ala Leu Leu Gln Tyr Glu Arg Pro
                515                 520                 525

Asp Asp Pro Gln Ile Ile Lys Gly Ile Arg Phe Leu Ile Asp Glu His
                530                 535                 540

Glu Ser Ser Arg Glu Arg Leu Glu Tyr Pro Thr Gly Ile Gly Leu Pro
545                 550                 555                 560

Asn Gln Phe Tyr Ile Arg Tyr His Ser Tyr Pro Phe Val Phe Ser Leu
                565                 570                 575

Leu Ala Ser Ser Ala Phe Ile Lys Lys Ala Glu Met Arg Glu Thr Tyr
                580                 585                 590

<210> SEQ ID NO 18
<211> LENGTH: 631
<212> TYPE: PRT
<213> ORGANISM: Alicyclobacillus acidocaldarius

<400> SEQUENCE: 18

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
                35                  40                  45

Leu Cys His Ile Leu Asp Arg Val Asp Arg Asp Arg Met Glu Lys Ile
                50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
                100                 105                 110

Ala Leu Arg Phe Ile Gln Ser Gln Gly Gly Ile Glu Ser Ser Arg Val
                115                 120                 125

Phe Thr Arg Met Trp Leu Ala Leu Val Gly Glu Tyr Pro Trp Glu Lys
                130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala

-continued

```
            165                 170                 175
Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Arg Arg Arg
            195                 200                 205

Gly Ala Lys Gly Gly Gly Trp Ile Phe Asp Ala Leu Asp Arg Ala
            210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
            245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
            290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
            325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
            370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
            405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
            450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
            485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
            530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
            565                 570                 575

Gly Val Gln Tyr Leu Val Glu Thr Gln Arg Pro Asp Gly Gly Trp Asp
            580                 585                 590
```

```
Glu Pro Tyr Tyr Thr Gly Thr Gly Phe Pro Gly Asp Phe Tyr Leu Gly
        595             600             605
Tyr Thr Met Tyr Arg His Val Phe Pro Thr Leu Ala Leu Gly Arg Tyr
        610             615             620
Lys Gln Ala Ile Glu Arg Arg
625             630
```